US010865188B2

(12) United States Patent
Seiders et al.

(10) Patent No.: US 10,865,188 B2
(45) **Date of Patent: *Dec. 15, 2020**

(54) DIBENZO AZEPINE COMPOUNDS AND THEIR USE IN THE TREATMENT OF OTIC DISEASES AND DISORDERS

(71) Applicant: Pipeline Therapeutics, Inc., San Diego, CA (US)

(72) Inventors: Thomas Jon Seiders, San Diego, CA (US); Catherine Yuling Lee, San Diego, CA (US); Yiwei Li, Potomac, MD (US)

(73) Assignee: Pipeline Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/292,050

(22) Filed: Mar. 4, 2019

(65) Prior Publication Data

US 2019/0194140 A1 Jun. 27, 2019

Related U.S. Application Data

(63) Continuation of application No. 15/950,065, filed on Apr. 10, 2018, now Pat. No. 10,301,266, which is a continuation of application No. PCT/US2016/059194, filed on Oct. 27, 2016.

(60) Provisional application No. 62/248,625, filed on Oct. 30, 2015.

(51) Int. Cl.

| | |
|---|---|
| ***C07D 223/20*** | (2006.01) |
| ***A61K 47/34*** | (2017.01) |
| ***A61K 9/00*** | (2006.01) |
| ***A61K 47/02*** | (2006.01) |
| ***A61K 47/10*** | (2017.01) |
| ***C07D 223/18*** | (2006.01) |
| ***A61K 47/36*** | (2006.01) |
| ***A61K 47/38*** | (2006.01) |
| ***A61K 47/32*** | (2006.01) |
| ***A61P 27/16*** | (2006.01) |

(52) U.S. Cl.

CPC .......... *C07D 223/20* (2013.01); *A61K 9/0046* (2013.01); *A61K 47/02* (2013.01); *A61K 47/10* (2013.01); *A61K 47/32* (2013.01); *A61K 47/34* (2013.01); *A61K 47/36* (2013.01); *A61K 47/38* (2013.01); *A61P 27/16* (2018.01); *C07D 223/18* (2013.01); *C07B 2200/13* (2013.01)

(58) Field of Classification Search

CPC .. C07D 223/18; C07D 223/20; A61K 9/0046; A61K 47/36; A61K 47/47–34; A61K 47/32; A61K 47/38; A61K 47/02; A61K 47/10; A61P 27/16; C07B 2200/13

See application file for complete search history.

(56) References Cited

U.S. PATENT DOCUMENTS

| | | | | |
|---|---|---|---|---|
| 5,059,591 | A | 10/1991 | Janoff et al. | |
| 7,160,875 | B2 | 1/2007 | Flohr et al. | |
| 7,166,587 | B2 | 1/2007 | Flohr et al. | |
| 10,301,266 | B2 * | 5/2019 | Seiders | A61K 47/36 |
| 2005/0054633 | A1 * | 3/2005 | Flohr | C07D 223/16 514/212.04 |
| 2005/0075327 | A1 * | 4/2005 | Flohr | C07D 243/12 514/212.04 |
| 2010/0016450 | A1 | 1/2010 | Lichter et al. | |
| 2012/0277199 | A1 | 11/2012 | Ye et al. | |
| 2015/0209367 | A1 | 7/2015 | Edge | |
| 2018/0273483 | A1 | 9/2018 | Seiders | |
| 2019/0307746 | A1 * | 10/2019 | Lorrain | A61K 31/5517 |

FOREIGN PATENT DOCUMENTS

| | | |
|---|---|---|
| EA | 009940 | 4/2008 |
| WO | WO 14/039781 | 3/2015 |

OTHER PUBLICATIONS

Brien, 1993, Ototoxicity associated with salicylates: a brief review, Drug Safety, 9(2):143-148.

Brittain ed., 2008, Polymorphism in Pharmaceuticals, 2nd ed.

Brittain, 2008, Preparation and identifcation of polymorphs and solvatemorphs, in Prefomulation in Solid Dosage Form Development, M.C. Adeyeye et al., eds., pp. 185-228.

Campbell, , 1998, Essential Audiology for Physicians, Delmar, Cengage Learning, Clifton Park, NY.

Datta et al., 2004, 3 Nature Reviews, Drug Discovery, pp. 42-57.

Izumikawa et. al., 2005, Auditory Hair Cell Replacement and Hearing Improvement by Atoh1 Gene Therapy in Deaf Mammals, Nat. Med., 11(3):271-276.

Liu et al., 2013, Current strategies for drug delivery to the inner ear, Acta Pharmaceutica Sinica B, 13(2):86-96.

Mizutari et. al., Jan. 9, 2013, Notch Inhibition Induces Cochlear Hair Cell Regeneration and Recovery of Hearing after Acoustic Trauma, Neuron, 77:58-69.

Oshima et al., 2009, Chapter 9: Isolation of sphere-forming stem cells from the mouse inner ear, in Sokolowski ed., Auditory and Vestibular Research: Methods and Protocols, Humana Press, New York, NY, pp. 141-162.

Ronaghi et al., 2014, Inner ear hair cell-like cells from human embryonic stem cells, Stem Cells Dev. 23(11):1275-1284.

Solid State Characterization of Pharmaceuticals, 473-492, 490, Storey et al., eds., 2011.

(Continued)

*Primary Examiner* — Mark L Shibuya
*Assistant Examiner* — Ebenezer O Sackey
(74) *Attorney, Agent, or Firm* — Mintz, Levin, Cohn, Ferris, Glovsky and Popeo, P.C.

(57) ABSTRACT

The present disclosure provides crystalline Compound I and crystalline Compound II, pharmaceutical compositions comprising one of said crystalline compounds suitable for intratympanic administration, and methods for treating otic disorders using the crystalline compounds and the pharmaceutical compositions.

24 Claims, 6 Drawing Sheets

(56) References Cited

OTHER PUBLICATIONS

Swan et al., 2008, Inner ear drug delivery for auditory applications, Adv. Drug Deliv. Rev., 60(15):1583-1599.
Yamamoto et al., 2006, Inhibition of Notch/RBP-J Signaling Induces Hair Cell Formation in Neonate Mouse Cochleas, J Mol Med, 84(1):37-45.
Yuan et al., Mar. 2, 2011, Cell-surface marker signatures for the isolation of neural stem cells, glia and neurons derived from human pluripotent stem cells, PLoS ONE, 6(3):e17540.
Zheng et al., 2000, Hes1 is a Negative Regulator of Inner Ear Hair Cell Differentiation, Development, 127(21):4551-4560.
Zine et al., 2001, Hes1 and Hes5 Activities Are Required for the Normal Development of the Hair Cells in the Mammalian Inner Ear, J Neurosci., 21(13):4712-4720.
International Search Report and Written Opinion dated Dec. 16, 2016 in PCT/US2016/059194.
Braga et al., 2009, Crystal polymorphism and multiple crystal forms, Struct Bond, 123:25-50.
Hilfiker, ed., 2006, Polymorphism: in the Pharmaceutical Industry, Wiley-VCH Verlag GmbH & Co. Weinheim, Germany.
Karagianni et al., 2018, Co-amorphous solid dispersions for solubility and absorption improvement of drugs: composition, preparation, characterization and formulations for oral delivery, Pharmaceutics, 10(98), 26 pp.
Laitinen et al., 2013, Emerging trends in the stabilization of amorphous drugs, International Journal of Pharmaceutics, 453:65-79.
CAS Registry No. 209984-57-6, Product Information LY411575, Cayman Chemical (Jul. 22, 2014). Located at <https://www.caymanchem.com/pdfs/16162.pdf> 1 page.

* cited by examiner

XRPD Diffractogram of Crystalline Compound I

XRPD Diffractogram of Crystalline Compound II

DIBENZO AZEPINE COMPOUNDS AND THEIR USE IN THE TREATMENT OF OTIC DISEASES AND DISORDERS

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/950,065, filed Apr. 10, 2018, which is a continuation of PCT International Application No. PCT/US2016/059194, filed Oct. 27, 2016, which claims the benefit of priority to U.S. Provisional Patent Application No. 62/248,625 filed Oct. 30, 2015. Each of the aforementioned applications is incorporated by reference herein in its entirety, and each is hereby expressly made a part of this specification.

BACKGROUND

Field

The present disclosure is directed to the use of certain substituted dibenzo azepine derivatives and pharmaceutical compositions thereof in the treatment of otic diseases and disorders of the inner ear. The present disclosure is further directed to pharmaceutical compositions and methods of treating otic diseases and disorders.

Description

Hearing loss afflicts over ten percent of the population of the United States. Damage to the peripheral auditory system is responsible for a majority of such hearing deficits. In particular, destruction of hair cells and destruction of the primary afferent neurons in the spiral ganglia, which transduce auditory signals from the hair cells to the brain, have been implicated as major causes of hearing impairments.

Agents causing hearing impairment include loud noise, aging, infections, and ototoxic chemicals. Among the last are certain therapeutic drugs, contaminants in foods or medicines, and environmental and industrial pollutants. Therapeutic agents that have been found to have adverse effect on hearing include aminoglycoside antibiotics (such as streptomycin, neomycin, gentamicin, kanamycin, tobramycin and amikacin), platinum-containing antineoplastic agents such as cisplatin and carboplatin, certain macrolide antibiotics such as erythromycin, glycopeptide antibiotics such as vancomycin, quinine and its analogs, salicylate and its analogs, and loop diuretics such as furosemide and ethacrynic acid. Ototoxins such as cisplatin and aminoglycoside antibiotics accumulate in cochlear hair cells, and cellular damage to these cells resulting from the accumulation is thought to be the primary reason for chemically-induced hearing loss. The vestibular and auditory systems share many characteristics including peripheral neuronal innervations of hair cells and central projections to the brainstem nuclei. Vestibular functions are similarly sensitive to ototoxins as described above.

The toxic effects of these drugs on auditory cells and spiral ganglion neurons are often the limiting factor in their therapeutic usefulness. For example, the aminoglycoside antibiotics are broad spectrum antimicrobials effective against gram-positive, gram-negative and acid-fast bacteria. They are used primarily to treat infections caused by gram-negative bacteria, often in combination with beta lactams which provide synergistic effects. Advantages to using the aminoglycoside antibiotics include a low incidence of *Clostridium difficile* diarrhea relative to other antibiotics, and a low risk of allergic reactions. However, the aminoglycosides are known to exhibit serious ototoxicity, especially at higher doses. For example, 25% of patients given one gram of streptomycin daily for 60 to 120 days displayed some vestibular impairment, whereas at two grams per day, the incidence increased to 75%, and some patients suffer permanent damage (see U.S. Pat. No. 5,059,591).

Salicylates, such as aspirin, have long been used for their anti-inflammatory, analgesic, anti-pyretic and anti-thrombotic effects. Unfortunately, salicylates have ototoxic side effects, often leading to tinnitus ("ringing in the ears") and temporary hearing loss, and if used at high doses for a prolonged time, hearing impairment can become persistent and irreversible (J. A. Brien, 1993, Drug Safety 9:143-148).

Loop diuretics (such as ethacrynic acid, furosemide, and bumetanide) are known to cause ototoxicity. Several less-commonly used loop diuretics also have been experimentally shown to cause ototoxicity; this group includes torsemide, azosemide, ozolinone, indacrinone, and piretanide. Hearing loss associated with loop diuretics is frequently, but not always, reversible.

Ototoxicity is a serious dose-limiting side-effect for cisplatin, a widely-used antineoplastic agent that has proven effective on a variety of human cancers including testicular, ovarian, bladder, and head and neck cancers. The toxic side effects of cisplatin (peripheral neuropathies, myelo-suppression, gastrointestinal toxicity, nephrotoxicity, and ototoxicity) are well-known. The routine administration of mannitol, hypertonic saline, and high fluid administration have largely ameliorated cisplatin-induced nephrotoxicity, leaving ototoxicity as the primary dose-limiting factor today. Thus, although an increasing number of cancer patients are surviving modem regimens of chemotherapy, they frequently suffer from cisplatin-induced hearing impairment.

Cisplatin damages both the auditory and vestibular systems. The primary ototoxic effects of cisplatin appear to occur in the cochlea. Anatomical changes occur in both the stria vascularis and the organ of Corti. The primary histologic findings include dose-related hair cell degeneration and damage to the supporting cells, and at high doses, total collapse of the membranous labyrinth can occur. In the organ of Corti, there is loss of outer and inner hair cells, with a propensity for outer hair cell loss in the basal turn, and alterations in the supporting cells and Reissner's membrane. Softening of the cuticular plate and an increased number of lysosomal bodies in the apical portion of the outer hair cell have also been reported.

Noise-induced hearing loss (NIHL) describes a chronic hearing-impairing disease process that occurs gradually over many years of exposure to less intense noise levels, wherein the damage is to the inner ear, specifically, the cochlea. This type of hearing loss is generally caused by chronic exposure to high intensity continuous noise with superimposed episodic impact or impulse noise. Both an intense sound presented to the ear for a short period of time and a less intense sound that is presented for a longer time period will produce equal damage to the inner ear. The majority of chronic NIHL is due to occupational or industrial exposure. However, a non-occupational form of NIHL, called socioacusis, may result from gunfire, loud music (via concerts or headphones), open vehicles such as motorcycles, snowmobiles or tractors, and power tools to name just a few. Although the hearing damage is often symmetrical, i.e. both ears are affected, there are cases, such as hearing loss due to frequent target shooting, which result asymmetric hearing loss.

Upon exposure to impulse noise, such as an explosive blast, a patient may suffer significant tympanic membrane and middle ear damage. In chronic exposure, which generally occurs at lower intensity levels, middle ear and tympanic membrane damage are unlikely. In noise exposure, the primary and initial damage is generally cochlear, with secondary neural degeneration of the auditory system occurring over time. Noise-induced hearing loss has been reviewed by K. Campbell in "Essential Audiology for Physicians" (1998), San Diego: Singular Publishing Group, Inc.

Age-related hearing loss, or presbycusis, is a common neurodegenerative disorder in aged adults. Approximately one in three people in the United States between the ages of 65 and 74 has hearing loss, and nearly half of those older than 75 have difficulty hearing (data from National Institution on Deafness and other Communication Disorders). The process of aging interacts with many other factors, such as noise exposure and miscellaneous ototoxic insults which are hazardous to the receptor hair cells (HC) and the spiral ganglion neurons (SGNs) in the cochlea. In many cases, it is difficult to distinguish between the effects of aging per se and the effects of other hazardous factors on cell death in the cochlea. Permanent hearing loss resulting from the loss of HCs and SGNs is irreversible because the cells are terminally developed and cannot be replaced by mitosis.

Otitis media is an inflammation of the middle ear, most commonly associated with viral or bacterial infection. A relatively high percentage of the population, particularly children, are affected. In children, the disease is most often associated with upper respiratory afflictions which trigger a transudate secretion response in the Eustachian tube and middle ear. Bacteria and viruses migrate from the nasopharynx to the normally air-filled middle ear via the Eustachian tube, and can cause the Eustachian tube to become blocked, preventing ventilation and drainage of the middle ear. Fluid then accumulates behind the eardrum, causing pain and inflammation.

Otitis media is the most common cause of hearing loss among children. Although otitis media is readily treated with antibiotics and is ordinarily not serious, frequent and/or untreated otitis media may permanently damage a child's hearing. Fluid remaining in the middle ear can cause repeated bouts of acute otitis media, and if the condition becomes chronic it may result in frequent recurrences of acute infections. In the more severe forms of otitis media, purulent exudate, toxins and endogenous anti-microbial enzymes accumulate in the middle ear, which can cause irreparable damage to sensory-neural and sound conducting structures. Damage to the eardrum, the bones of the ear, or the auditory nerves caused by such infections can potentially lead to permanent hearing loss. Hearing loss may also result from impairment, damage or destruction of inner ear cochlear hair cells, as damaging substances in the middle ear space gain access to the inner ear via diffusion through the round window membrane.

Izumikawa, M., et. al., "Auditory Hair Cell Replacement and Hearing Improvement by Atohl Gene Therapy in Deaf Mammals", Nat. Med. 11(3), 271-276 (2005), discloses that administration of the Atohl gene via an adenovector to the cochlea improved the hearing threshold in guina pigs. Notch signaling pathway inhibitors, and in particular, selective gamma secretase inhibitors are understood to stimulate hair cell differentiation through their positive effect on expression of the Atohl. (Zheng et al., "Hes1 is a Negative Regulator of Inner Ear Hair Cell Differentiation", Development, 2000, 127(21):4551-60; Zine et al., "Hes1 and Hes5 Activities Are Required for the Normal Development of the Hair Cells in the Mammalian Inner Ear", J Neurosci., 2001, 21(13):4712-20; Yamamoto et al., "Inhibition of Notch/RBP-J Signaling Induces Hair Cell Formation in Neonate Mouse Cochleas", J Mol Med, 2006, 84(1):37-45).

Mizutari, K., et. al., "Notch Inhibition Induces Cochlear Hair Cell Regeneration and Recovery of Hearing after Acoustic Trauma", Neuron 77, 58-69 (2013), described a study of LY411575 in young mice with noise-induced hearing loss.

Applicants have identified selected substituted dibenzo azepine derivatives, which are especially suited to the task of the treating (including the prevention, reducing the incidence and/or severity, slowing or halting the progression and reversal) of otic diseases and disorders of the inner ear.

SUMMARY

The present disclosure provides crystalline forms of a compound selected from Compound I having the formula:

Compound I

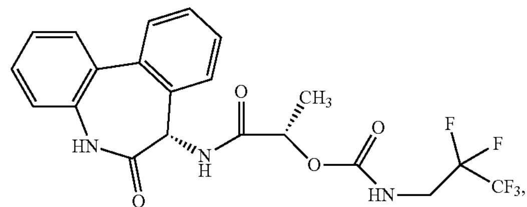

and Compound II having the formula:

Compound II

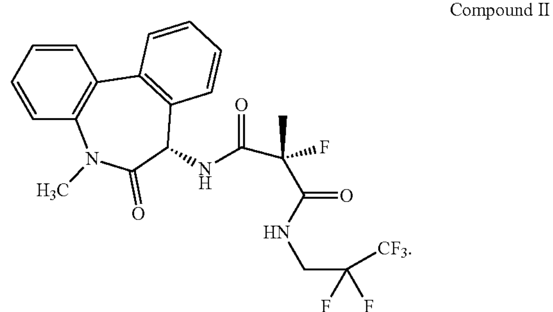 [SMILES: CN1C(=O)[C@@H](NC(=O)[C@](C)(F)C(=O)NCC(F)(F)C(F)(F)F)c2ccccc2-c2ccccc21]

In some embodiments the instant crystalline Compound I is characterized by an x-ray powder diffraction pattern with peaks at 8.2, 13.8, 14.0, 18.4, and 20.9±0.15 degrees two-theta.

In some embodiments the instant crystalline Compound I is characterized by an x-ray powder diffraction pattern with peaks at 4.6, 8.2, 9.2, 13.8, 14.0, 18.2, 18.4, 20.9, 23.8, and 27.7±0.15 degrees two-theta.

In some embodiments the instant crystalline Compound I is characterized by an x-ray powder diffraction pattern with peaks at 3.0, 4.6, 8.2, 9.2, 10.4, 13.8, 14.0, 16.4, 18.2, 18.4, 18.8, 19.1, 20.9, 21.5, 22.2, 22.7, 23.0, 23.8, 24.3, 24.7, 25.2, 26.5, 26.6, 27.1, 27.7, 28.1, 28.3, 28.6, 29.0, 30.0, 31.2, 31.5, 31.8, 32.1, 32.4, 35.1, 35.6, 35.8, 36.4, 36.7, 38.4, 38.8, 39.8, 40.5, and 40.8±0.15 degrees two-theta.

In some embodiments the instant crystalline Compound I is further characterized as having a differential scanning calorimetry endotherm onset at about 238.5° C. In some embodiments the instant crystalline Compound I is further characterized as having a differential scanning calorimetry endotherm peak at about 249.3° C.

In some embodiments the instant crystalline Compound II is characterized by an x-ray powder diffraction pattern with peaks at 8.4, 15.2, 16.0, 20.6, and 22.6±0.15 degrees two-theta.

In some embodiments the instant crystalline Compound II is characterized by an x-ray powder diffraction pattern with peaks at 6.5, 8.4, 15.2, 16.0, 19.9, 20.6, 22.6, 24.5, 25.1, and 30.6±0.15 degrees two-theta.

In some embodiments the instant crystalline Compound II is characterized by an x-ray powder diffraction pattern with peaks at 6.5, 8.4, 10.1, 13.1, 14.6, 15.0, 15.2, 16.0, 17.6, 18.0, 18.4, 19.6, 19.9, 20.1, 20.6, 20.9, 21.2, 22.2, 22.6, 23.3, 23.5, 23.8, 24.5, 24.9, 25.1, 25.8, 26.1, 26.7, 26.8, 27.5, 27.8, 29.6, 30.6, 31.2, 32.3, 32.9, 33.2, 33.9, 34.4, 35.4, 36.3, 36.7, 37.3, 37.7, 38.0, 38.9, 40.0, 40.2, 40.8, and 41.6±0.15 degrees two-theta.

In some embodiments the crystalline form of Compound II is further characterized as having a differential scanning calorimetry endotherm onset at about 173° C.

In some embodiments the crystalline form of Compound II is further characterized as having a differential scanning calorimetry endotherm peak at about 175° C.

In some embodiments the present disclosure provides an aqueous pharmaceutical composition for intratympanic administration comprising:

(1) an active agent selected from the crystalline Compound I and crystalline Compound II of the embodiments provided above, and (2) a pharmaceutically acceptable aqueous solution comprising:

(A) approximately 15% to 25% by weight (w/w) of poloxamer 407; or (B) (i) approximately 15% to 25% by weight (w/w) of poloxamer 407 and (ii) approximately 0.5% to 4% by weight (w/w) of hydroxypropyl methylcellulose having a nominal viscosity of 40-60 cP or grade 80-120 cP; or (C) (i) approximately 10%-20% by weight (w/w) of poloxamer 407, and (ii) approximately 0.1%-0.3% by weight (w/w) of Carbopol® 974P; or (D) (i) approximately 0.5% to 8% by weight (w/w) of a hyaluronic acid; or (E) (i) approximately 0.5% to 4% by weight (w/w) of a hyaluronic acid, and (ii) approximately 5% to 20% by volume of polyethylene glycol 400;

wherein said active agent is present in approximately 0.01% to about 20% w/v of said aqueous solution.

In some embodiments of the aqueous pharmaceutical composition the aqueous solution comprises:

(A) approximately 15% to 25% by weight (w/w) of poloxamer 407; or (B) (i) approximately 15% to 25% by weight (w/w) of poloxamer 407 and (ii) approximately 0.5% to 4% by weight (w/w) of hydroxypropyl methylcellulose having a nominal viscosity of 40-60 cP or grade 80-120 cP; or (C) (i) approximately 10%-20% by weight (w/w) of poloxamer 407, and (ii) approximately 0.1%-0.3% by weight (w/w) of Carbopol® 974P.

In some embodiments of the aqueous pharmaceutical composition said aqueous solution comprises approximately 15% to 25% by weight (w/w) of poloxamer 407.

In some embodiments of the aqueous pharmaceutical composition the pH of said aqueous solution is between about 7.0 and 8.0.

In some embodiments of the aqueous pharmaceutical composition said aqueous solution further comprises a buffering agent.

In some embodiments of the aqueous pharmaceutical composition said aqueous solution further comprises a buffering agent selected from (i) sodium phosphate monobasic, sodium phosphate dibasic or a combination thereof; and (ii) tris(hydroxymethyl)aminomethane.

In some embodiments of the aqueous pharmaceutical composition said active agent is present in approximately 0.1% to 5% w/v.

In some embodiments of the aqueous pharmaceutical composition said aqueous solution comprises approximately 15% to 18% by weight (w/w) of poloxamer 407.

In some embodiments the aqueous pharmaceutical composition comprises: (1) crystalline Compound I described above, and (2) a pharmaceutically acceptable aqueous solution comprising approximately 15% to 25% by weight (w/w) of poloxamer 407, wherein the pH is between about 7.0 and 8.0; and wherein said crystalline Compound I is present in approximately 0.01% to 20% w/v of said aqueous solution. In some embodiments said aqueous solution comprises approximately 15% to 18% by weight of poloxamer 407. In some embodiments crystalline Compound I is present in approximately 0.1% to 5% w/v. In some embodiments said aqueous solution comprises approximately 15% to 18% by weight of poloxamer 407, and crystalline Compound I is present in approximately 0.1% to 5% w/v.

In some embodiments the aqueous pharmaceutical composition comprises: (1) crystalline Compound II described above, and (2) a pharmaceutically acceptable aqueous solution comprising approximately 15% to 25% by weight (w/w) of poloxamer 407, wherein the pH is between about 7.0 and 8.0; and wherein said crystalline Compound II is present in approximately 0.01% to 20% w/v of said aqueous solution. In some embodiments said aqueous solution comprises approximately 15% to 18% by weight of poloxamer 407. In some embodiments crystalline Compound II is present in approximately 0.1% to 5% w/v. In some embodiments said aqueous solution comprises approximately 15% to 18% by weight of poloxamer 407, and crystalline Compound II is present in approximately 0.1% to 5% w/v.

In some embodiments the present disclosure provides a method for the treatment of otic disorders which comprises intratympanic administration of a therapeutically effective amount of an active agent selected from the crystalline compounds disclosed herein to a patient in need thereof to an area at or near the round window membrane in the ear of said patient.

In some embodiments of the method of treating otic disorders, the otic disorder can be hearing loss.

In some embodiments, a method of treating an otic disorder is provided comprising intratympanic administration of an aqueous pharmaceutical composition described herein to a patient in need of such treatment to an area at or near the round window membrane in the ear of said patient. In some embodiments, the otic disorder can be hearing loss. In some embodiments, the aqueous pharmaceutical composition may be administered at a frequency of between once a week to once every 3 months.

In some embodiments, a method of treating hearing loss is provided comprising intratympanic administration to a patient in need of such treatment to an area at or near the round window membrane in the ear of said patient of an aqueous pharmaceutical composition comprising (1) an active agent selected from the crystalline compounds described herein; and (2) an aqueous solution comprising approximately 15% to 18% by weight (w/w) of poloxamer 407, wherein the pH is between approximately 7.0 and 8.0; and wherein said active agent is present in approximately 0.1% to 5% w/v. In some embodiments the active agent is crystalline Compound I as described herein. In some embodiments the active agent is crystalline Compound II as described herein.

Some embodiments of the present disclosure are directed to the use of an active agent selected from crystalline compounds disclosed herein or a composition comprising the same in the preparation of a medicament for the treatment of otic disorders. In some embodiments, the medicament is formulated for intratympanic administration to an area at or near the round window membrane in the ear of a patient. In some embodiments of the use, the otic disorder can be hearing loss.

Some embodiments of the present disclosure are directed to the use of an active agent selected from crystalline compounds disclosed herein or a composition comprising the same in the preparation of an aqueous pharmaceutical composition described herein for use in the treatment of an otic disorder. In some embodiments, the aqueous pharmaceutical composition is formulated for intratympanic administration to an area at or near the round window membrane in the ear of a patient. In some embodiments, the otic disorder can be hearing loss.

Some embodiments of the present disclosure are directed to the use an active agent selected from crystalline compounds disclosed herein or a composition comprising the same in the preparation of an aqueous pharmaceutical composition comprising (1) an active agent selected from a crystalline compound described herein; and (2) an aqueous solution comprising approximately 15% to 18% by weight (w/w) of poloxamer 407, wherein the pH is between approximately 7.0 and 8.0; and wherein said active agent is present in approximately 0.1% to 5% w/v in the treatment of hearing loss. In some embodiments, the aqueous pharmaceutical composition is formulated for intratympanic administration to an area at or near the round window membrane in the ear of a patient. In some embodiments the active agent is crystalline Compound I as described herein. In some embodiments the active agent is crystalline Compound II as described herein.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION

The term "Compound I" refers to the compound (2,2,3,3,3-pentafluoropropyl)-carbamic acid (S)-1-((S)-6-oxo-6,7-dihydro-5H-dibenzo[b,d]azepin-7-ylcarbamoyl) ethyl ester having the structure formula:

Compound I

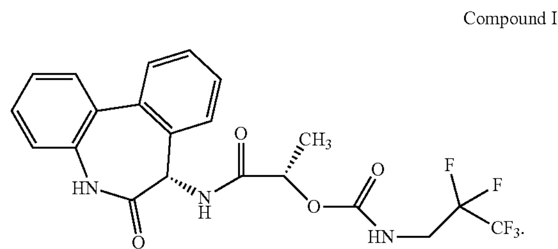 [SMILES: C[C@H](OC(=O)NCC(F)(F)C(F)(F)F)C(=O)N[C@@H]1C(=O)Nc2ccccc2-c2ccccc21]

The term "Compound II" refers to the compound (2R)-2-fluoro-2-methyl-N—[(S)-5-methyl-6-oxo-6,7-dihydro-5H-dibenzo[b,d]azepin-7-yl]-N'-(2,2,3,3,3-pentafluoropropyl)malonamide having the structure formula:

Compound II

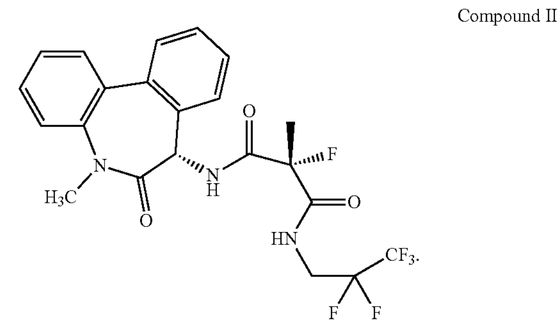 [SMILES: CN1C(=O)[C@@H](NC(=O)[C@](C)(F)C(=O)NCC(F)(F)C(F)(F)F)c2ccccc2-c2ccccc21]

Crystalline forms of Compound I and Compound II may be obtained by dissolving the corresponding amorphous material in an alcohol such as methanol or ethanol, and subsequently collecting the solids formed. The crystalline Compound I and Compound II were characterized using X-ray powder diffraction using a Bruker (Billerica, Mass.) AXS C2 GADDS diffractometer or a Bruker AXS D8 Advance utilizing copper K-alpha (40 kV, 40 mA) radiations. DSC data were collected on a Mettler (Columbus, Ohio) DSC 823E equipped with a 34 position auto-sampler. The instrument was calibrated for energy and temperature using certified indium. Typically 0.5-3 mg of each sample, in a pin-holed aluminium pan, was heated at 10° C./min from 25° C. to 300° C. A nitrogen purge at 50 ml/min was maintained over the sample.

Figure 3:
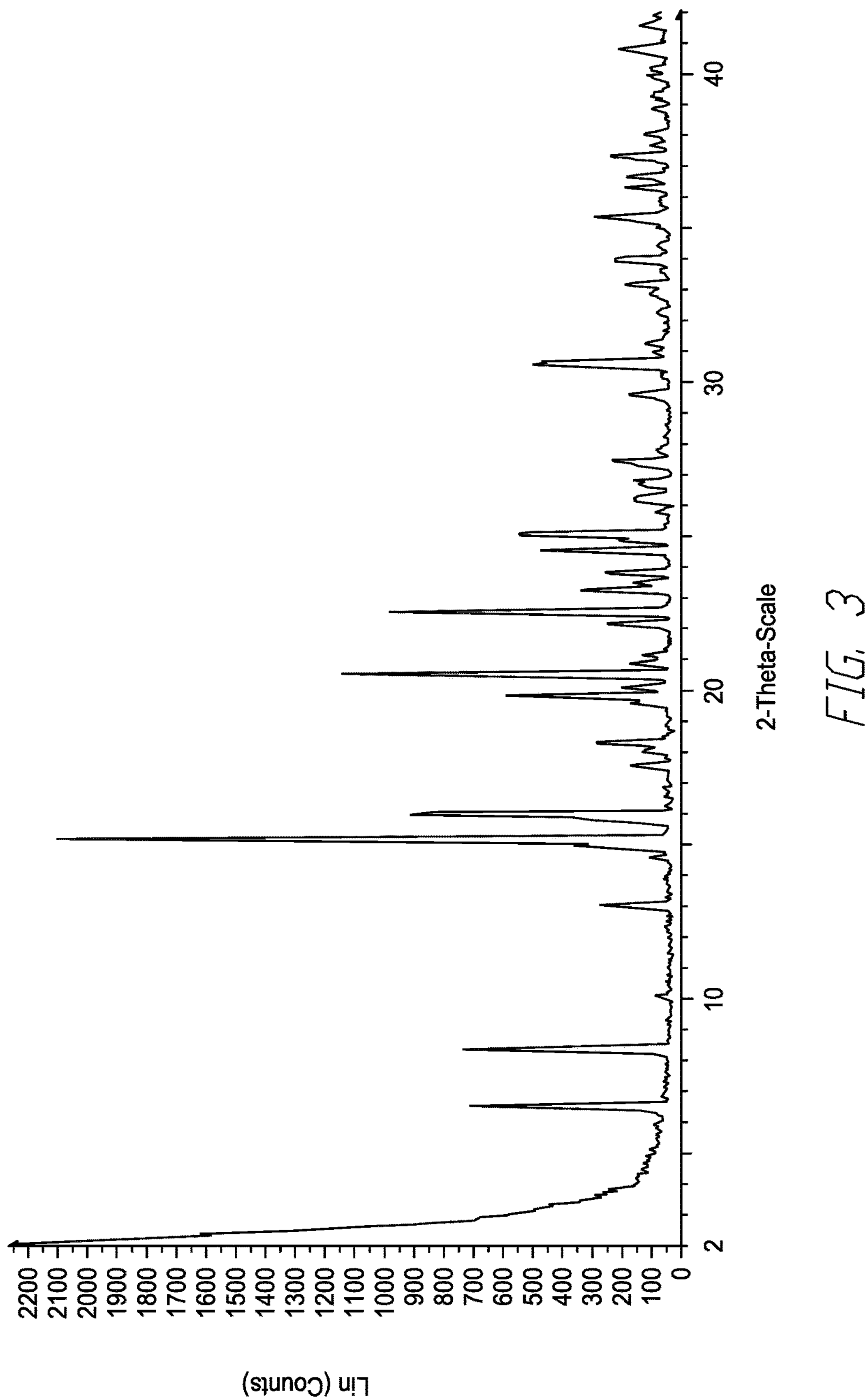
FIG. 3 depicts the x-ray powder diffraction diffractogram of crystalline Compound II.

Crystalline Compound I may be characterized by the Cu K-α x-ray powder diffraction (XRPD) pattern substantially as shown in FIG. 3. Alternatively, crystalline Compound I may be characterized by the x-ray powder diffraction pattern with peaks at about 8.2, 13.8, 14.0, 18.4, 20.9±0.15 degrees two-theta; or by the x-ray powder diffraction pattern with peaks at about 4.6, 8.2, 9.2, 13.8, 14.0, 18.2, 18.4, 20.9, 23.8, 27.7±0.15 degrees two-theta; or by the x-ray powder diffraction pattern with peaks at about 3.0, 4.6, 8.2, 9.2, 10.4, 13.8, 14.0, 16.4, 18.2, 18.4, 18.8, 19.1, 20.9, 21.5, 22.2, 22.7, 23.0, 23.8, 24.3, 24.7, 25.2, 26.5, 26.6, 27.1, 27.7, 28.1, 28.3, 28.6, 29.0, 30.0, 31.2, 31.5, 31.8, 32.1, 32.4, 35.1, 35.6, 35.8, 36.4, 36.7, 38.4, 38.8, 39.8, 40.5, 40.8±0.15 degrees two-theta. Alternatively, crystalline Compound I may be characterized as described in the Examples section, infra.

Figure 4:
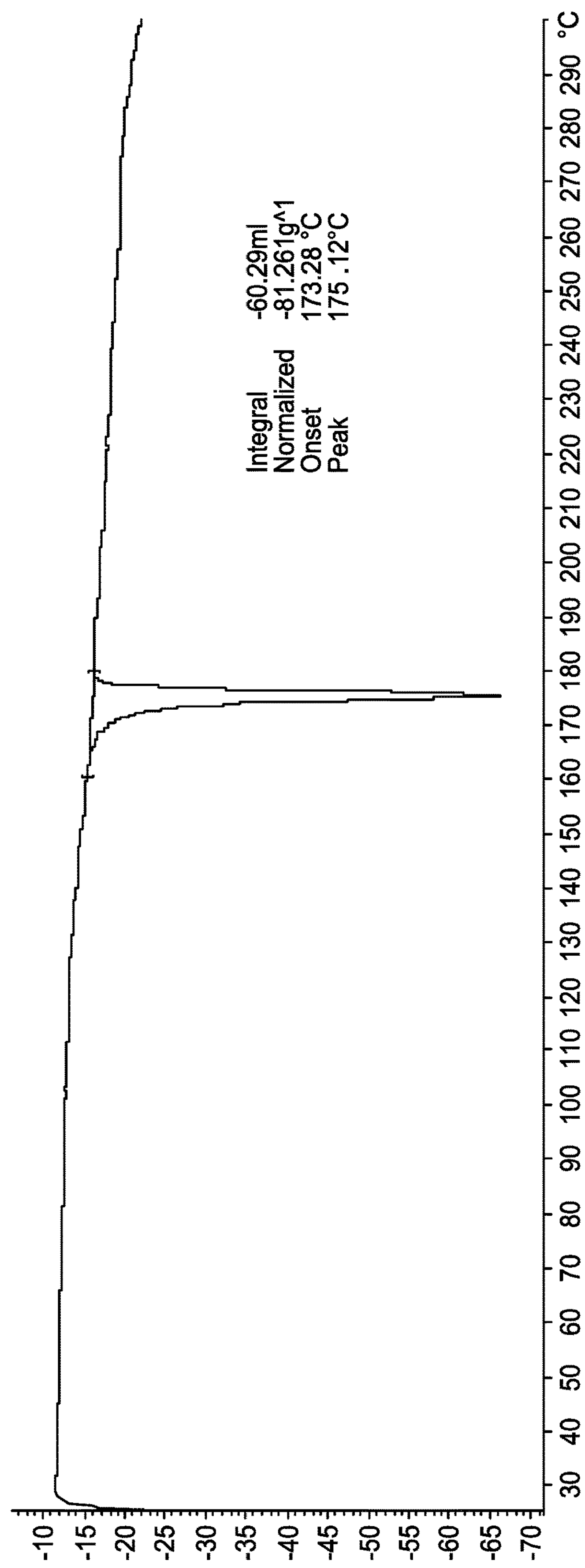
FIG. 4 depicts the Differential Scanning Calorimetry (DSC) curve for crystalline Compound II.

Crystalline Compound II may be characterized by the Cu K-α x-ray powder diffraction (XRPD) pattern substantially as shown in FIG. 4. Alternatively, crystalline Compound II may be characterized by the x-ray powder diffraction pattern with peaks at about 8.4, 15.2, 16.0, 20.6, 22.6±0.15 degrees two-theta; or by the x-ray powder diffraction pattern with peaks at about 6.5, 8.4, 15.2, 16.0, 19.9, 20.6, 22.6, 24.5, 25.1, 30.6±0.15 degrees two-theta; or by the x-ray powder diffraction pattern with peaks at about 6.5, 8.4, 10.1, 13.1, 14.6, 15.0, 15.2, 16.0, 17.6, 18.0, 18.4, 19.6, 19.9, 20.1, 20.6, 20.9, 21.2, 22.2, 22.6, 23.3, 23.5, 23.8, 24.5, 24.9, 25.1, 25.8, 26.1, 26.7, 26.8, 27.5, 27.8, 29.6, 30.6, 31.2, 32.3, 32.9, 33.2, 33.9, 34.4, 35.4, 36.3, 36.7, 37.3, 37.7, 38.0, 38.9, 40.0, 40.2, 40.8, 41.6±0.2. Alternatively, crystalline Compound II may be characterized as described in the Examples section, infra.

Crystalline Compound I and Compound II are useful in the preparation of aqueous pharmaceutical compositions for intratympanic administration as described herein. Crystalline Compound I and Compound II and the aqueous pharmaceutical compositions containing them are useful for the treatment of otic diseases and disorders.

Pharmaceutical Composition

In one aspect the present disclosure is directed to aqueous pharmaceutical compositions for intratympanic administration comprising an active agent selected from crystalline Compound I and crystalline Compound II, and a pharmaceutically acceptable aqueous solution. The active agents are Notch signaling pathway inhibitors, and in particular, are selective gamma secretase inhibitors.

In some embodiments, the active agent is selected from crystalline Compound I as described and characterized herein. In some embodiments the active agent is crystalline Compound II as described and characterized herein.

In some embodiments, the crystalline active agent is further processed to provide a more uniform particle size or to control the particle size or to reduce the particle size. For example, the initial crystalline material may be subject to mechanical impact means such as crushing, grinding, milling (such as ball milling and jet milling), and the like to provide particles having the desired particle size distribution.

In some embodiments the aqueous pharmaceutical compositions for intratympanic administration comprise provide sustained release of the active agent in the middle ear. Sustained release formulations typically include a polymer; suitable polymers for the present disclosure that may be mentioned include, but are not limited to, gelatin, hyaluronic acid/hyaluronates, chitosan, and polyoxyethylene-polyoxypropylene triblock copolymers [see e.g., Liu et al., Acta Pharmaceutica Sinica B, 2013, 13(2): 86-96, and Swan et al., Adv. Drug Deliv. Rev., 2008, 60(15): 1583-1599].

In some embodiments the present aqueous pharmaceutical compositions can be delivered to the middle ear as a lower viscosity liquid at ambient temperature which forms in situ a gel having a higher viscosity. The advantages of such a composition include (1) the convenience of handling a liquid at the time of administration, and (2) once gelled in situ a prolonged time of release of the drug at the site of deposit. Increasing the release time results in a prolonged time of therapeutic effectiveness and potentially lowered drug dose. Such compositions advantageously comprise a thermoreversible gel which has the property of being a liquid at ambient temperature and a gel at about mammalian body temperature.

Thermoreversible gels that are suitable for pharmaceutical application may be prepared using polymers including poly(lactic acid)-poly(ethylene glycol) (PLA-PEG) or triblock copolymers of PEG-PLGA-PEG. A chitosan-glycerolphosphate solution is able to form a reversible thermosetting gel. Addition of sugar-based phosphates transforms chitosan into a thermo-reversible gel drug delivery system. A common group of thermoreversible gels is polyoxyalkylene based polymers, such as the polyoxyethylene-polyoxypropylene triblock copolymers known generically as poloxamers. Poloxamers in aqueous solutions exhibit thermoreversible properties that are advantageous for the present disclosure. Thus, aqueous solutions of poloxamer can transition from liquid state to gel state with rising temperature. The liquid-gel transition temperature may be adjusted by varying the concentration of the poloxamer as well as addition of other excipients such as viscosity modifying agents; thus solutions of poloxamer may be prepared that are in liquid state at room temperature or below, and transition to gel state at body temperature. In one embodiment of the present composition, the thermoreversible gel is poloxamer 407 (e.g., Pluronic® F127 marketed by BASF, Florham Park, N.J.).

In some embodiments the present aqueous pharmaceutical composition for intratympanic administration comprising an active agent selected from crystalline Compound I and crystalline Compound II, and a pharmaceutically acceptable aqueous solution comprising poloxamer 407. The poloxamer may be present in a concentration from about 15 to about 25% by weight. In some embodiments the poloxamer 407 concentration is from about 15 to about 18% by weight. In some embodiment the poloxamer 407 concentration is from about 16 to about 17% by weight. In some embodiments the poloxamer is present in approximately 15 or 16 or 17 or 18% by weight. In some embodiments the pharmaceutical compositions of the present disclosure comprising poloxamer 407 may optionally include hydroxypropyl methylcellulose (HPMC) having a nominal viscosity of 40 to 120 cP, and in an amount approximately 0.5% to 4% by weight.

In some embodiments the composition of the present disclosure is an aqueous pharmaceutical composition for intratympanic administration comprising an active agent selected from crystalline Compound I and crystalline Compound II, and a pharmaceutically acceptable carrier comprising (a) approximately 0.5% to 8% by weight of a hyaluronic acid; or (b) (i) approximately 0.5% to 4% by weight of a hyaluronic acid, and (ii) approximately 5% to 20% by volume of polyethylene glycol 400 (PEG400).

In the aqueous pharmaceutical compositions for intratympanic administration the concentration of the active agent selected from crystalline Compound I and crystalline Compound II is generally from about 0.01% w/v to 20% w/v. This range includes the sub-range of about 0.05 w/v to about 15 w/v, about 0.1 w/v to about 10 w/v, about 0.1% w/v to about 5% w/v. In some embodiments the concentration of the active agent is from about 0.5% w/v to about 5% w/v. In some embodiments the concentration of the active agent is from about 0.5 to about 4% w/v. In some embodiments the concentration of the active agent is from about 1 to about 5% w/v. In some embodiments the concentration of the active agent is from about 1 to about to about 4%. In some embodiment the concentration of the active agent is about 0.5, 1.0, 1.5, 2.0, 2.5, 3.0, 3.5, 4.0, 4.5 or 5% w/v. In some embodiment the concentration of the active agent is about 0.1, 0.2, 0.3, 0.4, 0.5, 0.6, 0.7, 0.8, 0.9 or 1% w/v.

The composition disclosed herein may contain any conventional non-toxic pharmaceutically-acceptable excipients. In some embodiments, the pH of the composition is between about 6 to 8, or about 6 to 7, or about 7 to 8. In some embodiments the composition may include a buffer such as monosodium phosphate or disodium phosphate or a combination thereof and may be phosphate buffered saline (PBS), or a buffer such as tris(hydroxymethyl)aminomethane (TRIS). The amount of buffer may be from about 0.1 to about 0.5% by weight.

In some embodiments the aqueous pharmaceutical composition of the present disclosure may include a viscosity modifier such as Carbopol® 974P (Lubrizol Advanced Materials, Cleveland, Ohio). In some embodiments the aqueous pharmaceutical composition for intratympanic administration comprises an active agent selected from crystalline Compound I and crystalline Compound II, and a pharmaceutically acceptable carrier comprising poloxamer 407 and a viscosity modifier such as Carbopol® 974P. In some embodiments poloxamer 407 is present in approximately 10% to 20% by weight, and Carbopol® 974P is present in about 0.1% to about 0.3% by weight. In some embodiments the active agent is crystalline Compound I or crystalline Compound II. Other common excipients may include preservatives such as methylparaben, as well as sodium chloride to provide isotonicity. The compositions are formulated such that they provide sustained release of the active agent for a period sufficient to effectuate gamma secretase inhibition. The sustained inhibition of gamma secretase minimizes the frequency of administration to once weekly, biweekly, monthly, bimonthly, quarterly, semiannually, annually, etc. In some embodiments, the dosing frequency is once every two weeks, or twice a month, or monthly or once every other month, or quarterly.

The aqueous pharmaceutical composition disclosed herein comprising an active agent selected from crystalline Compound I and crystalline Compound II and a carrier may be prepared using conventional methods such as described in the Examples, and may be packaged for single dose use such as in a syringe or for multiple dose such as in a vial. Alternatively, the active agent component and the aqueous solution component may be packaged separately, in separate compartments or in separate containers, and are mixed prior to administration.

Illustrative examples of compositions suitable for local inner ear administration of compounds of the present disclosure are provided in the Examples section, infra.

Method of Treatment

In one aspect the present disclosure is directed to methods for the treatment of otic disorders comprising intratympanic administration of a therapeutically effective amount of an active agent selected from crystalline Compound I and crystalline Compound II to a patient in need thereof to an area at or near the round window membrane in the ear of said patient. The term "otic disorders" generally relates to conditions resulting from cochlear hair cell loss including, but is not limited to, hearing loss and deafness, as well as conditions associated with vestibular dysfunction, which may be manifested through symptoms such as dizziness, imbalance, vertigo, nausea, and fuzzy vision. Hearing loss or deafness may be due to ototoxic chemicals, excessive noise, and aging.

As used herein, the term "treatment" or "therapy" or "treating" and the like includes controlling, alleviating, reversing, or slowing the progression of the condition being treated; for example, reduction or halting of further hearing loss due to the above or other factors; and the restoration of hearing following the partial or profound hearing loss due to the above or other factors. Treatment also includes prevention (e.g., delaying the onset of or reducing the risk of developing) of hearing loss as well as prophylactic use such as before, during or after receiving ototoxic chemicals such as an aminoglycoside antibiotic such as gentamicin or a platinum chemotherapeutic agent such as cisplatin.

As used herein, the term "therapeutically effective amount" refers to an amount of the active agent sufficient to elicit a desired or beneficial effect in the disease or disorder being treated; for prophylaxis, it refers to an amount of the active agent sufficient to prevent the onset or lessen the effect of the disease or disorder. The amount to be used depends on the active agent chosen, the severity of the disease or disorder being treated, the route of administration and patient characteristics such as age.

In the present disclosure the active agent is administered to the ear by intratympanic injection into the middle ear, inner ear, or cochlea or combinations thereof. Intratympanic is also referred to as transtympanic, and both terms are used interchangeably herein. Intratympanic injection is the technique of injecting a therapeutic agent through the tympanic membrane into the middle ear where the therapeutic agent may diffuse across the round window membrane to reach the inner ear. It has been used in clinical practice for many years and is a relatively minor intervention which can be carried out in a doctor's office. For repeated injections, a middle ear ventilation tube may be inserted into the tympanic membrane, through which the medication can be administered into the middle ear space behind the tympanic membrane into the middle and/or inner ear. In one embodiment, the active agent is administered intratympanically to an area near or onto the round window membrane.

In some embodiments of the present method the active agent is administered in an aqueous pharmaceutical composition comprising a thermoreversible gel; such compositions are liquid at room temperature (for ease of administration) and turn into gel at body temperature such that the pharmaceutical composition does not quickly drain through the Eustachian tube. In some embodiments the present method utilizes the pharmaceutical compositions described hereinbelow.

Doses for local inner administration of crystalline Compound I or crystalline Compound II include from about 0.06 mg to about 100 mg. This range includes the sub-range of about 0.1 mg to about 90 mg, 0.25 mg to about 80 mg, 0.4 mg to 70 mg, 0.6 mg to 60 mg, 0.80 mg to 50 mg, 1.0 mg to 40 mg, 2 mg to 30 mg, 3 mg to 20 mg. The doses may be administered in an aqueous pharmaceutical composition comprising an aqueous solution, wherein the volume of aqueous solution to be administered comprises a range of about 100 μL to about 500 μL in volume. This range of volumes includes a sub-range of about 100 μL to 150 μL, 100 μL to 200 μL, 100 μL to 250 μL, 100 μL to 300 μL, 100 μL to 350 μL, 100 μL to 400 μL, 100 μL to 450 μL and 100 μL to 500 μL. This range of volumes also includes a sub-range of about 200 μL to 250 μL, 200 μL to 300 μL, 200 μL to 350 μL, 200 μL to 400 μL, 200 μL to 450 μL and 200 μL to 500 μL. This range of volumes also includes a sub-range of about 300 μL to 350 μL, 300 μL to 400 μL, 300 μL to 450 μL and 300 μL to 500 μL. This range of volumes also includes a sub-range of about 400 μL to 450 μL and 400 μL to 500 μL. Due to physical limitations, the proportion of the active agent to the aqueous pharmaceutical composition is contemplated to be 20% by weight or less.

In one aspect the compounds disclosed herein may be co-administered with one or more additional agents such as a steroid; for example, dexamethasone. In certain embodiments, the additional agents may be administered separately from crystalline Compound I or crystalline Compound II (e.g., sequentially, e.g., on different overlapping schedules). In other embodiments, these agents may be part of a single dosage form, mixed together with Compound I or Compound II in a single composition. In still another embodiment, these agents can be given as a separate dose that is administered at about the same time crystalline Compound I or crystalline Compound II is administered. When the compositions disclosed herein include a combination of a crystalline Compound I or crystalline Compound II and one or more additional therapeutic or prophylactic agents, both the compound and the additional agent can be present at dosage levels of between about 1 to 100%, and more preferably between about 5 to 95% of the dosage administered in a monotherapy regimen.

Biological Function

The utility of the present disclosure can be demonstrated by one or more of the following methods or other methods known in the art:

A. Otosphere Differentiation Assay

To determine compound activity in inducing mouse hair cell differentiation, otospheres were generated from the mouse organ of Corti as described in Oshima et al., Auditory and Vestibular Res Methods, 2009. Briefly, sensory epithelia from the neonatal organ of Corti were isolated, treated with trypsin, and gently dissociated. Dissociated cells were then transferred to a low adhesion well in DMEM/F12 media containing 1× B27 and N2 supplements (Invitrogen Life Sciences, Carlsbad, Calif.), EGF, IGF-1 and bFGF for sphere formation. After 3 days of sphere formation, spheres were isolated by centrifugation and transferred to fibronectin coated plates and allowed to adhere overnight in media lacking growth factors. Adherent spheres were then treated with the test compound at concentrations ranging from $10^{-5}$ to $10^{-10}$ M for 4d. RNA was then harvested with an RNeasy kit (Qiagen®, Hilden, Germany) and were analyzed using quantitative PCR performed using gene specific primers against Atohl and Myo7a using Rp119 as a housekeeping gene. Values were subsequently analyzed using the ΔΔCt method. Those of ordinary skill would understand that the ΔΔCt method is commonly used in the art of PCR.

B. Mouse Organ of Corti Explant Assay (a) Notch Inhibition.

Neonatal mouse explants were used to ascertain inhibition of the Notch pathway and to test compound ability to generate hair cells in an ex vivo system. Briefly, organ of Corti were dissected from postnatal day 3 mice and plated onto 4-well chambers coated with poly-L-lysine and fibronectin. Explants were plated directly into DMEM media containing 10% fetal bovine serum, B27 supplement with and without test compound. To ascertain Notch inhibition, RNA was extracted 24 h after compound addition using an RNeasy kit, and quantitative PCR performed using gene primers specific against Hes5. Rp119 was used as a housekeeping gene and values analyzed using the ΔΔCt method.

(b) Hair Cell Induction.

For hair cell induction studies, explants were generated and treated with the compound as above; however, explants were treated for 3-5 days with media replenished daily in the presence or absence of compound. Explants were then fixed with paraformaldehyde and immunostained with antibodies against MYO7A, SOX2 and counterstained with Alexa647-phalloidin and Hoechst. Images were taken on a Nikon N2 confocal system using NIS-Elements software (Nikon, Melville, N.Y., USA). MYO7A/phalloidin positive hair cells were then quantified and compared against vehicle treated groups.

C. Human Neural Stem Cell Assay

Neural stem cells (NSC) were derived from embryonic stem cells using a published protocol (Yuan et al., Mar. 2, 2011, PLoS ONE, 6(3):e17540). Cells were sorted and characterized at passage 3 and were expanded. Cells were then frozen at passage 5. Cells were maintained in NSC media (DMEM/F12, N2 (1×), B27(1×) (Invitrogen), and Pen/Strep (1×) (Life Technologies) with 20 ng/ml bFGF (BD Bioscience/Corning)). On day 1, cells were plated in 96 well plates that have been previously coated with poly-ornithin and laminin, 60,000 cells/well in 100 μl of media. On day 2, spent media was removed, and 180 μl of fresh media was added to the cells. Later that same day (day 2), cells were treated with 20 μl of NSC media containing test compounds (7 point CRC). On day 3, spent media was removed and 140 μl of RLT/bME was added to the cells. RNA was extracted using the QiaCube (Qiagen®, Germantown, Md., USA) using the total RNA extraction+DNAse protocol. RNA was then reverse-transcribed to cDNA using iScript (Bio-Rad, Hercules, Calif., USA). cDNA was then used for real-time PCR analysis using iTaq Sybergreen (BioRad). Expression of Atoh1, Hes5, Hes1, Myosin7a genes was evaluated using CFX96 or CFX384 (Bio-Rad). HPRT1 was used as a reference gene. Analysis was done using Microsoft® Excel® and CBIS (ChemInnovation Software, Inc., San Diego, Calif., USA).

The above procedure was followed to determine an $EC_{50}$ for each compound.

| Compound | hNSC Atoh1 $EC_{50}$ (μM) | hNSC HES1 $IC_{50}$ (μM) | hNSC HES5 $IC_{50}$ (μM) |
|---|---|---|---|
| I | 0.625 | 0.242 | 0.288 |
| II | 0.023 | | 0.023 |

D. Human Embryonic Stem Cell Differentiation to Hair Cell-Like Cells

This protocol was designed to differentiate human embryonic stem cells (hESCs) into otic progenitor cells and further differentiate the progenitor cells into hair cell-like cells. The hESCs were maintained on mitomycin C-treated mouse embryonic fibroblasts (MEFs) in knockout DMEM/F12 media supplemented with 20% knockout serum, lx non-essential amino acids, 1× 1-glutamine, 1× β-mercaptoethanol (bME) and 8-10 ng/ml human bFGF. The hESCs were passaged using collagenase onto new MEFs until they were ready to begin differentiation, in which case they were passaged onto matrigel coated plates in MEF-conditioned media supplemented with 8 ng/ml bFGF for 3-5 days.

Human ES cells were differentiated using a published protocol (Ronaghi M et al., Stem Cells Dev. 2014, 1275-84). With the exception that AggreWells plates (from Stem Cell Technology, Vancouver, Calif.) were used to generate embryoid bodies (EBs) in the first 6 days of the protocol. Treatment with potential Atohl or hair cell inducers was administered to the cells on day 34-39. On day 39, the cells were lysed for protein, fixed for imaging, or extracted for RNA as described below.

(a) Western Blot Analysis of Myosin7a:

Protein was simultaneously extracted from two experimentally similar wells using RIPA buffer. The protein concentration was determined using an established protocol, and a western blot was done with the differentiated protein samples, a sample of the hESCs of the same passage, a marker and a positive control cell sample that expresses Myosin7a (Y79 cells). The membrane was incubated with Myosin7a antibody as well as a α-actin antibody as loading control. Once the blot was imaged, Licor system was used to quantify the Myosin7a and α-actin bands for comparative analysis.

(b) Immunocytochemistry:

The wells were briefly rinsed with DPBS and then fixed for 10 minutes with 4% paraformaldehyde, followed by a 10 minute incubation with 100 mM glycine in DPBS. The wells were washed 3 times with DPBS, permeabilized for 10 minutes with 0.2% TritonX-100, and then blocked for one hour with buffer containing 0.1% BSA and 0.2% TritonX-100. Primary antibodies for Myosin7a and Sox2 were added and kept overnight at 4° C. The following day the wells were washed 3 times with DPBS and secondary antibodies were added and incubated in the dark at room temperature for 2 hours. The wells were washed 2 times and the cells were stained with 488-Phalloidin for 10 minutes in the dark at room temperature. The wells were washed 2 times with DPBS and Hoechst stain was added to the wells and incubated for 10 minutes in the dark at room temperature. The wells were washed a final 3 times and were imaged using the GE Healthcare Life Sciences (Pittsburgh, Pa., USA) InCell 2200 automated imaging system.

(c) PCR:

RNA was extracted and isolated using RNA isolation kit from Qiagen® (including DNAse treatment). RNA concentration was determined using the Nano-Drop. cDNA was made using iScript (Bio-Rad) on CFX96 (BioRad). The quantity of target genes such as Myosin7a, Atoh1, Hes5, Axin2 and GAPDH, was determined using the iTaq PCR kit (Bio-Rad) on a CFX-96 or CFX-384 real-time PCR (Bio-Rad). All primers were from OriGene (Rockville, Md.) or Integrated DNA Technologies (IDT, Coralville, Iowa).

E. Guinea Pig PK

Male Hartley guinea pigs (300-350 g) were anesthetized with ketamine and xylazine. Thirty microliters of an aqueous pharmaceutical composition of the instant embodiments was delivered transtympanically to deposit the drug to the round window membrane. Delivery was unilateral. The animals were placed in a warm chamber in a lateral recumbent position keeping the dosed ear side up until they recover from anesthesia.

At various timepoints after administration, the animals were euthanized by $CO_2$ inhalation. Blood and CSF were collected and stored at −80° C. The animals were decapitated, the temporal bones removed and the bulla opened to expose the otic capsule. Ipsilateral and contralateral perilymph were collected from the apex using a microcapillary tube. The ipsilateral cochlea was removed from the otic capsule and stored at −80° C. All tissues collected were analyzed using LC/MS/MS for test compound concentration as follows. Analytical standards were prepared by spiking known concentrations of the test compound stock solutions into matrices such as plasma or artificial CSF. Fixed amounts of tissues collected and spiked standards were precipitated with acetonitrile containing buspirone as an internal standard. The precipitated samples were centrifuged at 4000 g for 10 minutes at 4° C. The supernatants were analyzed using LC-MS/MS. The LC-MS/MS system was set up using the AB Sciex 4000 Qtrap (AB Sciex, Framingham, Mass.) equipped with Agilent 1200 series HPLC and CTC PAL Autosampler (Agilent Technologies, Santa Clara, Calif.).

F. Functional Pharmacodynamic (a) Surgical Delivery of Test Compound to the Round Window Membrane.

Surgery was performed on naïve mice or mice with noise or pharmacologically-damaged ears. The animals were anesthetized with isoflurane and an 8 mm retroauricular incision was made to the lower caudal edge of the pinna. The skin was retracted and the fatty tissue was blunt dissected away from where the facial nerve and muscle come together. The muscle was retracted to reveal an area in the tympanic bulla where the bone was thin. A 30 g needle was used to drill a hole in the exposed thin portion of the otic bulla. A Hamilton syringe equipped with a 32 g blunt needle was inserted into the opening of the otic bulla. The drug formulation was delivered by injection and the needle removed. Wound closure was made with tissue glue.

(b) Functional PD.

At various time points after drug delivery, typically 24 hours, the mice were euthanized by $CO_2$ exposure and the temporal bone was removed into ice cold RNAlater® (Thermo Fisher Scientific, Waltham, Mass., USA). The otic capsule was carefully dissected from the temporal bone, placed into a clean tube containing TriZol (Zymo Research, Irvine, Calif., USA), immediately flash frozen in liquid nitrogen and stored at −80° C. until RNA isolation. RNA was isolated using a Qiagen® RNA MiniElute kit according to manufacturer's instruction. cDNA was generated and PCR was performed on specific primers using BioRad iTaq.

G. Hair Cell Induction

In mice, the instant drug formulation was surgically delivered to the round window as described in Section F, above. In guinea pigs, the instant drug formulation was delivered via transtympanic injection to the round window niche as described in Section E, above. Seven to 14 days after drug delivery, the animals were euthanized with ketamine and xylazine, their whole body was perfused with 10% neutral buffered formalin and the temporal bones were removed and stored in formalin. For guinea pigs, when cochlea whole mounts were to be prepared, intrascalar perfusion was performed to fully bathe the cochlea in formalin. Midmodiolar sections or cochlea whole mounts were prepared and stained to identify hair cells.

H. Auditory Brainstem Response (ABR)

Naïve mice or mice at various times after either noise or pharmacological deafening were anesthetized with ketamine/xylazine/acepromazine and the auditory brainstem response was determined in both ears using a Tucker Davis (Alachua, Fla.) RZ6 apparatus. The mice were exposed to clicks or pure tones of 4, 8, 16, 24 and 32 kHz at 90-10 dB in 10 dB descending steps and the hearing threshold was determined.

The results of the above experiment performed using the formulations of Examples 3(c) and 3(d) are provided in the Table below:

| | ABR Threshold Improvement (dB) | | |
|---|---|---|---|
| | 16 kHz | 24 kHz | 32 kHz |
| Compound I | 7 | 10 | 8 |
| Compound II | 8 | 11 | 7 |

Guinea pigs, naïve or after pharmacological deafening, were anesthetized with ketamine/xylazine. The auditory brainstem response (ABR) was determined bilaterally using a Tucker Davis RZ6 apparatus. The guinea pigs were exposed to clicks or pure tones of 4, 8, 16 or 24 kHz at 90-10 dB in 10 dB descending steps and the hearing threshold was determined.

EXAMPLES

Example 1. Preparation of Crystalline Compound I

Figure 1:
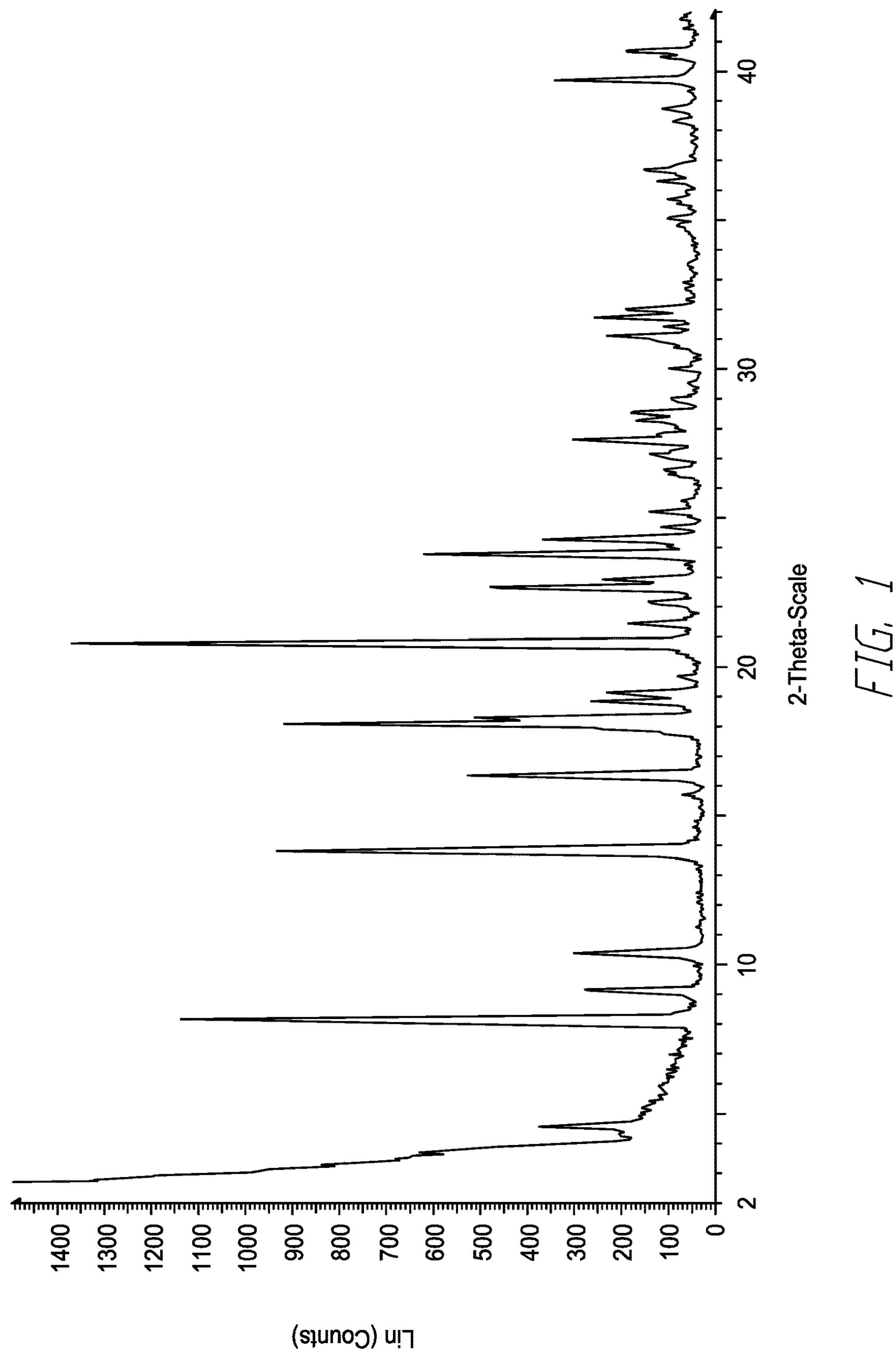
FIG. 1 depicts the x-ray powder diffraction diffractogram of crystalline Compound I.
Figure 2:
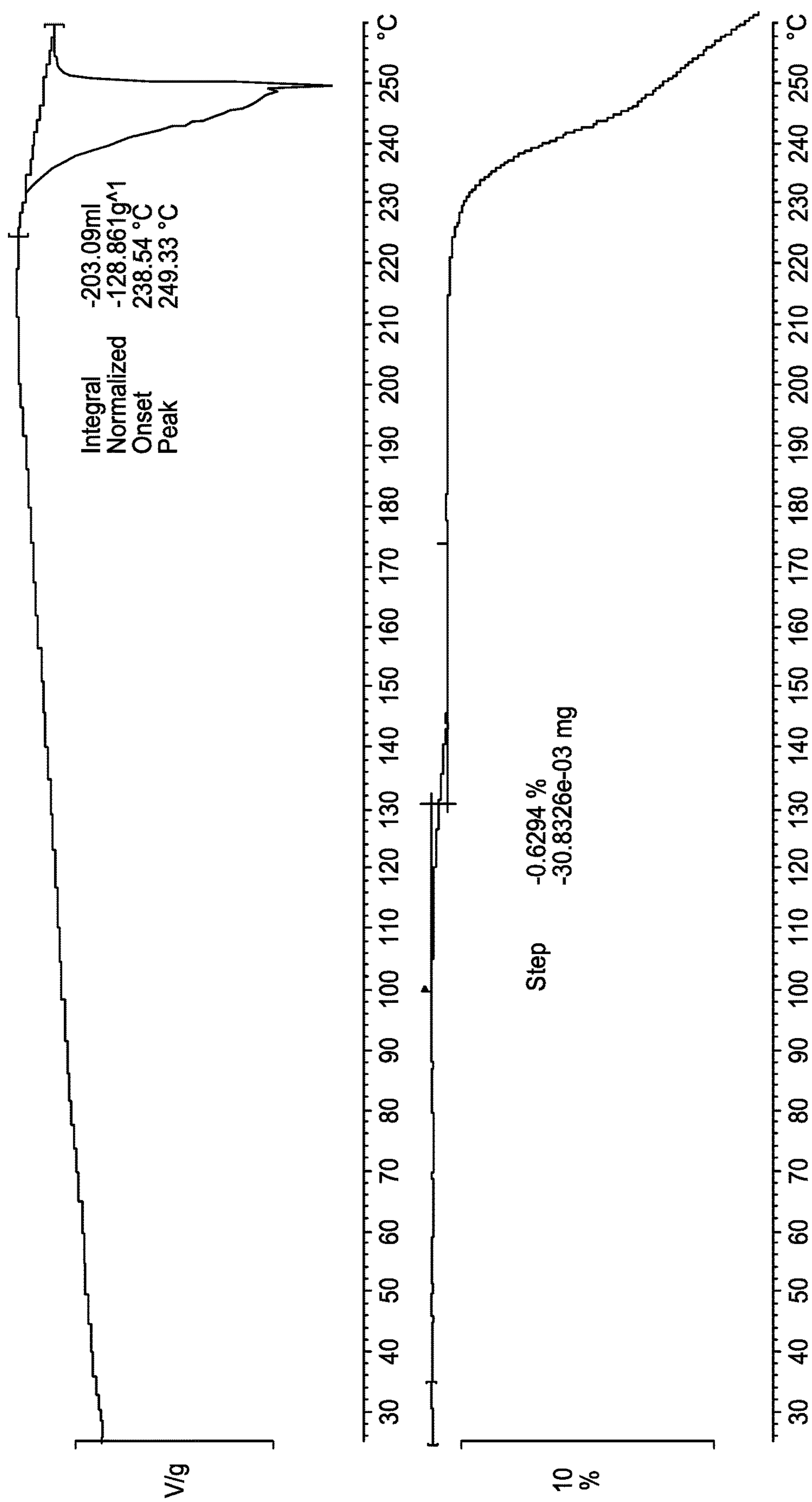
FIG. 2 depicts the Differential Scanning Calorimetry (DSC) curve for crystalline Compound I.

Compound I is disclosed in Flohr et al. U.S. Pat. No. 7,166,587, issued Jan. 23, 2007, and the synthetic procedure disclosed therein, when followed, produces Compound I as an amorphous material. Amorphous Compound I (2 g) was suspended in MeOH (60 mL) and the suspension was heated to 65 degrees C. to yield a clear solution. The solution was allowed to cool and remain at ambient temperature for 18 hours. During that time crystallization occurred. The reaction was filtered and the solid collected and dried under vacuum to yield a white solid (1 g) which was determined to be crystalline, and is characterized by the X-ray powder diffraction peaks in Table 1 and the pattern displayed in FIG. 1. DSC Endotherm onset occurs at 238.5° C. as shown in FIG. 2.

TABLE 1

XRPD peak locations for crystalline Compound I

| Peak | Angle (°2θ) | Intensity (counts) | Relative Intensity |
|---|---|---|---|
| 1 | 3.0 | 266 | 11.4 |
| 2 | 4.6 | 1173 | 50.3 |
| 3 | 8.2 | 2332 | 100.0 |
| 4 | 9.2 | 1038 | 44.5 |
| 5 | 10.4 | 410 | 17.6 |
| 6 | 13.8 | 1400 | 60.0 |
| 7 | 14.0 | 1342 | 57.5 |
| 8 | 16.4 | 859 | 36.8 |
| 9 | 18.2 | 1281 | 54.9 |
| 10 | 18.4 | 1352 | 58.0 |

TABLE 1-continued

XRPD peak locations for crystalline Compound I

| Peak | Angle (°2θ) | Intensity (counts) | Relative Intensity |
|---|---|---|---|
| 11 | 18.8 | 192 | 8.2 |
| 12 | 19.1 | 185 | 7.9 |
| 13 | 20.9 | 1427 | 61.2 |
| 14 | 21.5 | 152 | 6.5 |
| 15 | 22.2 | 193 | 8.3 |
| 16 | 22.7 | 335 | 14.4 |
| 17 | 23.0 | 548 | 23.5 |
| 18 | 23.8 | 840 | 36.0 |
| 19 | 24.3 | 296 | 12.7 |
| 20 | 24.7 | 144 | 6.2 |
| 21 | 25.2 | 145 | 6.2 |
| 22 | 26.5 | 143 | 6.1 |
| 23 | 26.6 | 151 | 6.5 |
| 24 | 27.1 | 112 | 4.8 |
| 25 | 27.7 | 680 | 29.2 |
| 26 | 28.1 | 147 | 6.3 |
| 27 | 28.3 | 127 | 5.4 |
| 28 | 28.6 | 202 | 8.7 |
| 29 | 29.0 | 86 | 3.7 |
| 30 | 30.0 | 87 | 3.7 |
| 31 | 31.2 | 459 | 19.7 |
| 32 | 31.5 | 139 | 6.0 |
| 33 | 31.8 | 371 | 15.9 |
| 34 | 32.1 | 279 | 12.0 |
| 35 | 32.4 | 121 | 5.2 |
| 36 | 35.1 | 137 | 5.9 |
| 37 | 35.6 | 146 | 6.3 |
| 38 | 35.8 | 172 | 7.4 |
| 39 | 36.4 | 137 | 5.9 |
| 40 | 36.7 | 166 | 7.1 |
| 41 | 38.4 | 98 | 4.2 |
| 42 | 38.8 | 136 | 5.8 |
| 43 | 39.8 | 362 | 15.5 |
| 44 | 40.5 | 133 | 5.7 |
| 45 | 40.8 | 353 | 15.1 |

Example 2. Preparation of Crystalline Compound II

Compound II is disclosed in Flohr et al. U.S. Pat. No. 7,160,875, issued Jan. 9, 2007, and the synthetic procedure disclosed therein, when followed, produces Compound II as an amorphous material. Amorphous Compound II (432 mg) was weighed into a 20 mL vial and dissolved in EtOH (2.15 mL, 5 volumes). The resulting clear solution was checked after 30 minutes and a white powder was observed to have formed. This suspension was agitated for approximately 16 hours at room temperature and the solid was isolated by filtration and was dried for 16 hours at 40° C./3 mbar to give a powdery white solid (315 mg, 73% yield) which was determined to be crystalline, and is characterized by the XRPD peaks in Table 2 and the pattern displayed in FIG. 3. DSC endotherm onset begins at 173° C. (melt) as shown in FIG. 4.

TABLE 2

XRPD peak locations for crystalline Compound II.

| Peak | Angle (°2θ | Intensity (counts) | Relative Intensity | Peak | Angle (°2θ) | Intensity (counts) | Relative Intensity |
|---|---|---|---|---|---|---|---|
| 1 | 6.5 | 711 | 33.7 | 26 | 25.8 | 84 | 4.0 |
| 2 | 8.4 | 737 | 35.0 | 27 | 26.1 | 155 | 7.4 |
| 3 | 10.1 | 85 | 4.0 | 28 | 26.7 | 141 | 6.7 |
| 4 | 13.1 | 277 | 13.1 | 29 | 26.8 | 158 | 7.5 |
| 5 | 14.6 | 101 | 4.8 | 30 | 27.5 | 231 | 11.0 |
| 6 | 15.0 | 353 | 16.7 | 31 | 27.8 | 79 | 3.7 |
| 7 | 15.2 | 2108 | 100.0 | 32 | 29.6 | 171 | 8.1 |
| 8 | 16.0 | 912 | 43.3 | 33 | 30.6 | 498 | 23.6 |

TABLE 2-continued

| XRPD peak locations for crystalline Compound II. | | | | | | | |
|---|---|---|---|---|---|---|---|
| Peak | Angle (°2θ | Intensity (counts) | Relative Intensity | Peak | Angle (°2θ) | Intensity (counts) | Relative Intensity |
| 9 | 17.6 | 170 | 8.1 | 34 | 31.2 | 119 | 5.6 |
| 10 | 18.0 | 129 | 6.1 | 35 | 32.3 | 79 | 3.7 |
| 11 | 18.4 | 286 | 13.6 | 36 | 32.9 | 100 | 4.7 |
| 12 | 19.6 | 168 | 8.0 | 37 | 33.2 | 191 | 9.1 |
| 13 | 19.9 | 592 | 28.1 | 38 | 33.9 | 219 | 10.4 |
| 14 | 20.1 | 202 | 9.6 | 39 | 34.4 | 77 | 3.7 |
| 15 | 20.6 | 1146 | 54.4 | 40 | 35.4 | 293 | 13.9 |
| 16 | 20.9 | 179 | 8.5 | 41 | 36.3 | 193 | 9.2 |
| 17 | 21.2 | 126 | 6.0 | 42 | 36.7 | 178 | 8.4 |
| 18 | 22.2 | 245 | 11.6 | 43 | 37.3 | 234 | 11.1 |
| 19 | 22.6 | 987 | 46.8 | 44 | 37.7 | 103 | 4.9 |
| 20 | 23.3 | 342 | 16.2 | 45 | 38.0 | 122 | 5.8 |
| 21 | 23.5 | 162 | 7.7 | 46 | 38.9 | 96 | 4.6 |
| 22 | 23.8 | 253 | 12.0 | 47 | 40.0 | 114 | 5.4 |
| 23 | 24.5 | 476 | 22.6 | 48 | 40.2 | 100 | 4.7 |
| 24 | 24.9 | 210 | 10.0 | 49 | 40.8 | 210 | 10.0 |
| 25 | 25.1 | 540 | 25.6 | 50 | 41.6 | 139 | 6.6 |

Examples 3(a) and 3(b) Preparation of Formulation A-1

Example 3(a)—To 128 mL sterile filtered water was added 0.9 g sodium chloride, 0.59 g sodium phosphate dibasic, and 0.17 g sodium phosphate monobasic. The solution was stirred at ambient temperature and 27.2 g poloxamer 407 was added and stirred overnight to yield a clear solution. 2 mL of the solution described above was added to 40 mg of crystalline Compound I and the suspension was stirred on an ice bath for 20 minutes to yield a homogeneous suspension.

Example 3(b)—A homogeneous suspension containing 2% w/v crystalline Compound II was prepared in the same manner as described above.

Examples 3(c) and (d) of Formulation A-2

Example 3(c)—To 129 mL sterile water was added 0.96 g sodium chloride, 0.59 g sodium phosphate dibasic, and 0.14 g sodium phosphate monobasic. The solution was stirred at ambient temperature and 25.6 g poloxamer 407 was added and stirred overnight to yield a clear solution. The solution was sterile filtered and 1 mL of the solution described above was added to 20 mg of crystalline Compound I and the suspension was vortexed for 60 minutes to yield a homogeneous suspension.

Example 3(d)—A homogeneous suspension containing 2% w/v crystalline Compound II was prepared in the same manner as described above.

Example 4. Preparation of Formulation B

To 3 mL of sterile filtered 0.1 M pH7 TRIS buffer was added 0.6 g of poloxamer 407 and this was stirred overnight at 4° C. to form a clear, homogeneous solution. To this solution was then added 60 mg of crystalline Compound I and 3 mg of methylparaben. The resulting suspension was stirred at 4° C. for 16 hours and stored at 4° C. until dosing.

Examples 5(a), 5(b), 5(c) and 5(d). Preparation of Formulation C

Example 5(a)—To 10 mL of sterile filtered 0.1 M pH 7 TRIS buffer was added 1.8 g of poloxamer 407 and this was stirred overnight at 4° C. to form a clear, homogeneous solution. To 3 mL of this solution was then added 60 mg of crystalline Compound I, and the suspension was stirred overnight at 4° C. to form a homogeneously-distributed suspension. Finally, 90 mg of hydroxypropyl methylcellulose (HPMC) (40-60 cp) (Sigma-Aldrich, St. Louis, Mo.) and 3 mg of methylparaben were added and the suspension was stirred at 4° C. for 16 hours and stored at 4° C. until dosing.

Example 5(b)—A homogeneous suspension containing 2% of amorphous Compound I was prepared following the procedure described above.

Example 5(c)—A homogeneous suspension containing 2% of crystalline Compound II was prepared following the procedure described above.

Example 5(d)—A homogeneous suspension containing 2% of amorphous Compound II was prepared following the procedure described above.

Example 6. Preparation of Formulation D

To 3 mL of sterile filtered 0.1 M pH 7 TRIS buffer was added 0.54 g of poloxamer 407 and this was stirred overnight at 4° C. to form a clear, homogeneous solution. To this solution was then added 60 mg of crystalline Compound I and the suspension was stirred overnight at 4° C. to form a homogeneously-distributed suspension. Finally, 90 mg of HPMC (40-60 cp), 3 mg of methylparaben and 6 mg of Carbopol® 974P (Lubrizol Advanced Materials, Cleveland, Ohio) were added and the suspension was stirred at 4° C. for 16 h and stored at 4° C. until dosing.

Example 7. Preparation of Formulation E

To 3 mL of sterile filtered 0.1 M pH 7 TRIS buffer was added 0.54 g of poloxamer 407 and this was stirred overnight at 4° C. to form a clear, homogeneous solution. To this solution was then added 60 mg of crystalline Compound I and the suspension was stirred overnight at 4° C. to form a homogeneously-distributed suspension and stored at 4° C. until dosing.

Example 8. Preparation of Formulation F

To 10 mL of sterile filtered phosphate buffer saline was added 100 mg of hyaluronic acid and this was stirred at the ambient temperature overnight to form a clear, homogeneous solution. To 60 mg of crystalline Compound I was added 0.6 mL of PEG400 (Sigma-Aldrich, St. Louis, Mo.). The suspension was stirred at ambient temperature. 3 mL of the hyaluronic acid solution described above was added to the Compound I and PEG400 suspension. The suspension was stirred at ambient temperature to form a homogeneously-distributed suspension.

Example 9. Preparation of Formulation G

To 10 mL of sterile filtered phosphate buffer saline was added 200 mg of hyaluronic acid and this was stirred at the ambient temperature overnight to form a clear, homogeneous solution. To 60 mg of crystalline Compound I was added 0.15 mL of PEG400. The suspension was stirred at ambient temperature. 3 mL of the hyaluronic acid solution described above was added to the Compound I and PEG400 suspension. The suspension was stirred at ambient temperature to form a homogeneously-distributed suspension.

Examples 10(a) and 10(b). Preparation of Formulation H

Example 10(a)—To 10 mL of sterile filtered phosphate buffer saline was added 150 mg of hyaluronic acid and this was stirred at the ambient temperature overnight to form a clear, homogeneous solution. To 60 mg of crystalline Compound I was added 0.3 mL of PEG400. The suspension was stirred at ambient temperature. 3 mL of the hyaluronic acid solution described above was added to the Compound I and PEG400 suspension. The suspension was stirred at ambient temperature to form a homogeneously-distributed suspension.

Example 10(b)—A homogeneous suspension containing 2% of crystalline Compound II was prepared following the procedure described above.

Example 11. Preparation of Formulation I

To 5 mL of sterile filtered phosphate buffer saline was added 50 mg of Oligopeptide (Corning® PuraMatrix™ Peptide Hydrogel, Corning, N.Y.) and this was stirred at the ambient temperature for 2 hours to form a clear, homogeneous solution. To 60 mg of crystalline Compound I was added 0.3 mL of PEG400. The suspension was stirred at ambient temperature. 3 mL of the Oligopeptide solution described above was added to the Compound I and PEG400 suspension. The suspension was stirred at ambient temperature to form a homogeneously-distributed suspension.

Example 12. Preparation of Formulation J

To 5 mL of sterile filtered phosphate buffer saline was added 500 mg of HPMC (40-60 cp) and this was stirred at the ambient temperature for overnight to form a clear, homogeneous solution. To 60 mg of crystalline Compound I was added 0.3 mL of PEG400. The suspension was stirred at ambient temperature. 3 mL of the HPMC solution described above was added to the Compound I and PEG400 suspension. The suspension was stirred at ambient temperature to form a homogeneously-distributed suspension.

Example 13. Guinea Pig PK

Liquid compositions described herein were evaluated using the method described in Part E of the Biological Function section provided above. The liquid compositions prepared as described in Example 5(a)-5(d) were each drawn into a 1 mL syringe. Using the filled 1 mL syringe, the liquid composition was back-filled at 5° C. into a 100 μL Hamilton syringe adapted with 28 gauge needle. The Hamilton syringe was then allowed to warm to room temperature.

Male Hartley guinea pigs (300-350 g) were anesthetized with ketamine and xylazine. Thirty microliters of the above liquid composition were delivered transtympanically to deposit the drug to the round window membrane. The delivery was unilateral. The animals were placed in a warm chamber in a lateral recumbent position keeping the dosed ear side up until they recovered from anesthesia.

At various timepoints after administration, the animals were euthanized by $CO_2$ inhalation. Blood and cerebrospinal fluid were collected and stored at −80° C. The animals were decapitated, the temporal bones removed and the bulla were opened to expose the otic capsule. Ipsilateral and contralateral perilymph were collected from the apex using a micro-capillary tube. The ipsilateral cochlea was removed from the otic capsule and was stored at −80° C. All tissues collected were analyzed using LC/MS/MS as described in Part E of the Biological Function section above.

Figure 5A:
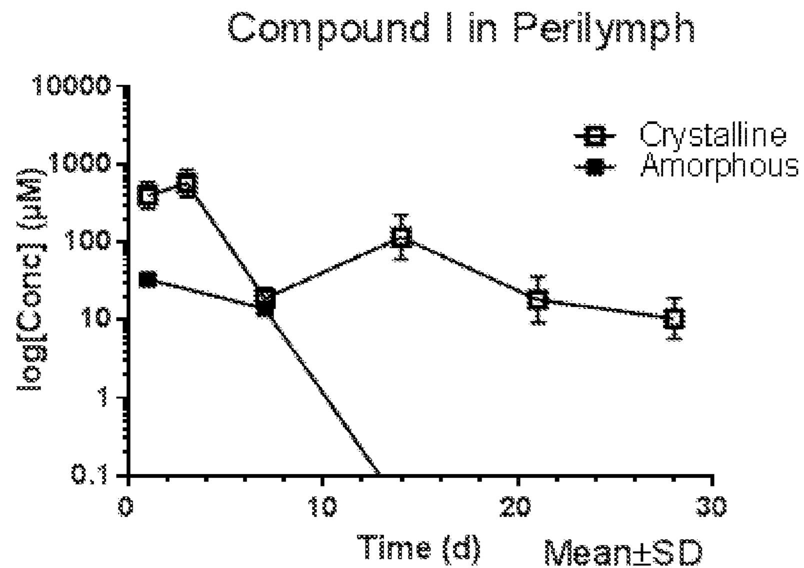
FIG. 5A depicts Guinea Pig PK in the perilymph for an aqueous pharmaceutical composition comprising Compound I in amorphous form and in crystalline form.
Figure 5B:
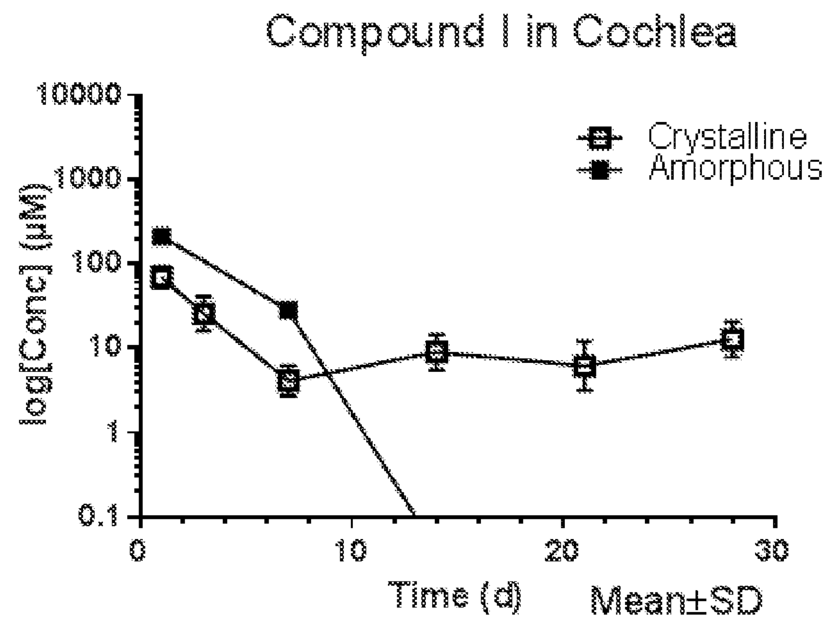
FIG. 5B depicts Guinea Pig PK in the cochlea for an aqueous pharmaceutical composition comprising Compound I in amorphous form and in crystalline form.
Figure 6A:
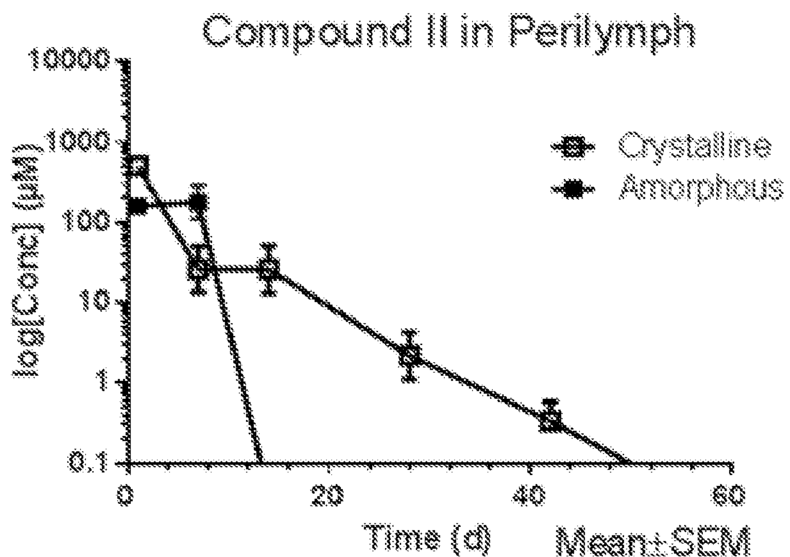
FIG. 6A depicts Guinea Pig PK in the perilymph for an aqueous pharmaceutical composition comprising Compound II in amorphous form and in crystalline form.
Figure 6B:
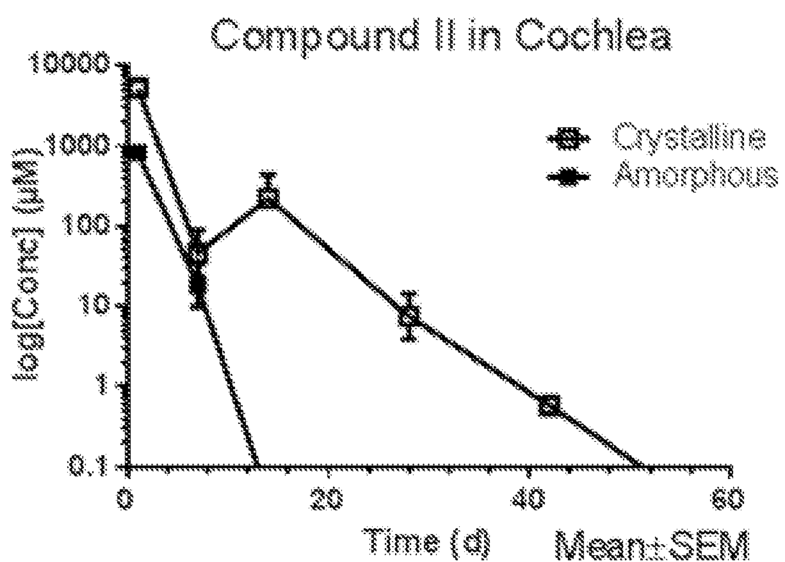
FIG. 6B depicts Guinea Pig PK in the cochlea for an aqueous pharmaceutical composition comprising Compound II in amorphous form and in crystalline form.

The concentrations of Compound I and Compound II were measured using LC/MS/MS in both the perilymph fluid and the cochlea tissue after a transtympanic injection of an instant formulation of either the crystalline form or the amorphous form at various time points. When dosed as the amorphous form, the concentration of Compound I in the perilymph and the cochlea was above the human NSC $EC_{50}$ for Atoh1 at 1 day and 7 days. The concentration of Compound 1 when dosed as the crystalline form was above the NSC $EC_{50}$ from day 1 to day 28. When dosed as the amorphous form, the concentration of Compound II in perilymph and cochlea was above the human NSC $EC_{50}$ for Atoh1 at 1 day and 7 days. The concentration of Compound II when dosed as crystalline form was above the human NSC $EC_{50}$ Atoh1 from day 1 to day 42. Concentration of the instant compounds in the perilymph and/or cochlea tissue was above the human NSC $EC_{50}$ for Atoh1, an indicator that the subject compounds may be efficacious in hair cell regeneration and hearing restoration in human. Surprisingly, the pK results show formulations containing crystalline Compound I and crystalline Compound II provide longer exposure of Compound I and Compound II to the inner ear than formulations containing the respective amorphous forms. Table 3 below lists the results for the studies using aqueous formulations of crystalline Compound I while Table 4 below lists those for aqueous formulations of crystalline Compound II. The results for aqueous formulations of crystalline Compound I are also graphically shown in FIG. 5A and FIG. 5B while the results for aqueous formulations of crystalline Compound II are graphically shown in FIG. 6A and FIG. 6B.

TABLE 3

| | Crystalline | | Amorphous | |
|---|---|---|---|---|
| Day | Perilymph Average (μM) (n = 6) | Cochlea Average (μM) | perilymph Average (μM) (n = 3) | Cochlea Average (μM) (n = 3) |
| 1 | 394.7 | 69.0 (n = 3) | 33.3 | 211.2 |
| 3 | 568.5 | 25.6 (n = 3) | | |
| 7 | 18.9 | 4.1 (n = 6) | 14.0 | 28.4 |
| 14 | 116.0 | 9.0 (n = 6) | 0.0 | 0.04 |

TABLE 3-continued

| | Crystalline | | Amorphous | |
|---|---|---|---|---|
| Day | Perilymph Average (μM) (n = 6) | Cochlea Average (μM) | perilymph Average (μM) (n = 3) | Cochlea Average (μM) (n = 3) |
| 21 | 18.2 | 6.2 (n = 6) | | |
| 28 | 10.4 | 12.8 (n = 6) | | |

LLOQ = 0.08 μM

TABLE 4

| | Crystalline | | Amorphous | |
|---|---|---|---|---|
| Day | Perilymph Average (μM) (n = 3) | Cochlea Average (μM) (n = 3) | perilymph Average (μM) (n = 3) | Cochlea Average (μM) (n = 3) |
| 1 | 501.6 | 5282.0 | 159.4 | 829.2 |
| 7 | 26.0 | 46.1 | 178.4 | 18.1 |
| 14 | 26.0 | 221.7 | 0.0 | 0.0 |
| 28 | 2.2 | 7.6 | 0.0 | 0.0 |
| 42 | 0.3 | 0.6 | | |
| 56 | 0.0 | 0.0 | | |

LLOQ = 0.08 μM

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. Crystalline Compound I having the formula:

Compound I

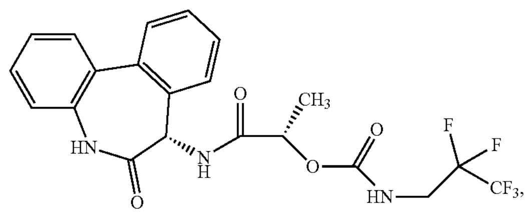

characterized by an x-ray powder diffraction pattern with peaks at 8.2, 13.8, 14.0, 18.4, and 20.9±0.15 degrees two-theta; and characterized as having a differential scanning calorimetry endotherm onset at about 238.5° C.

2. Crystalline Compound I, according to claim 1, characterized by an x-ray powder diffraction pattern with peaks at 4.6, 8.2, 9.2, 13.8, 14.0, 18.2, 18.4, 20.9, 23.8, and 27.7±0.15 degrees two-theta.

3. Crystalline Compound I, according to claim 1, characterized by an x-ray powder diffraction pattern with peaks at 3.0, 4.6, 8.2, 9.2, 10.4, 13.8, 14.0, 16.4, 18.2, 18.4, 18.8, 19.1, 20.9, 21.5, 22.2, 22.7, 23.0, 23.8, 24.3, 24.7, 25.2, 26.5, 26.6, 27.1, 27.7, 28.1, 28.3, 28.6, 29.0, 30.0, 31.2, 31.5, 31.8, 32.1, 32.4, 35.1, 35.6, 35.8, 36.4, 36.7, 38.4, 38.8, 39.8, 40.5, and 40.8±0.15 degrees two-theta.

4. Crystalline Compound II having the formula:

Compound II

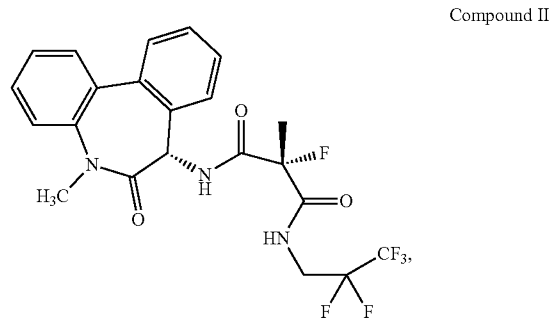 [SMILES: CN1C(=O)[C@@H](NC(=O)[C@](C)(F)C(=O)NCC(F)(F)C(F)(F)F)c2ccccc2-c2ccccc21]

characterized by an x-ray powder diffraction pattern with peaks at 8.4, 15.2, 16.0, 20.6, and 22.6±0.15 degrees two-theta; and characterized as having a differential scanning calorimetry endotherm onset at about 173° C.

5. Crystalline Compound II, according to claim 4 characterized by an x-ray powder diffraction pattern with peaks at 6.5, 8.4, 15.2, 16.0, 19.9, 20.6, 22.6, 24.5, 25.1, and 30.6±0.15 degrees two-theta.

6. Crystalline Compound II, according to claim 4, characterized by an x- ray powder diffraction pattern with peaks at 6.5, 8.4, 10.1, 13.1, 14.6, 15.0, 15.2, 16.0, 17.6, 18.0, 18.4, 19.6, 19.9, 20.1, 20.6, 20.9, 21.2, 22.2, 22.6, 23.3, 23.5, 23.8, 24.5, 24.9, 25.1, 25.8, 26.1, 26.7, 26.8, 27.5, 27.8, 29.6, 30.6, 31.2, 32.3, 32.9, 33.2, 33.9, 34.4, 35.4, 36.3, 36.7, 37.3, 37.7, 38.0, 38.9, 40.0, 40.2, 40.8, and 41.6±0.15 degrees two-theta.

7. An aqueous pharmaceutical composition comprising:

(1) an active agent selected from:

a crystalline Compound I having the formula:

Compound I

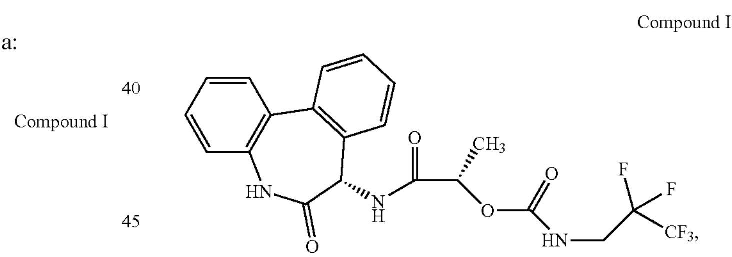

characterized by an x-ray powder diffraction pattern with peaks at 8.2, 13.8, 14.0, 18.4, and 20.9±0.15 degrees two-theta; or a crystalline Compound II having the formula:

Compound II

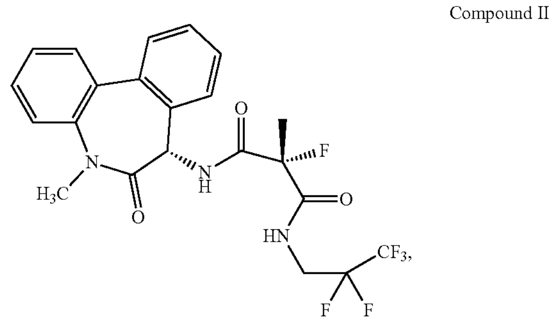 [SMILES: CN1C(=O)[C@@H](NC(=O)[C@](C)(F)C(=O)NCC(F)(F)C(F)(F)F)c2ccccc2-c2ccccc21]

characterized by an x-ray powder diffraction pattern with peaks at 8.4, 15.2, 16.0, 20.6, and 22.6±0.15 degrees two-theta; and (2) a pharmaceutically acceptable aqueous solution.

8. The aqueous pharmaceutical composition according to claim 7 wherein said aqueous solution comprises:

(A) approximately 15% to 25% by weight (w/w) of poloxamer 407; or (B) (i) approximately 15% to 25% by weight (w/w) of poloxamer 407 and (ii) approximately 0.5% to 4% by weight (w/w) of hydroxypropyl methylcellulose having a nominal viscosity of 40-60 cP or grade 80-120 cP; or (C) (i) approximately 10%-20% by weight (w/w) of poloxamer 407, and (ii) approximately 0.1%-0.3% by weight (w/w) of Carbopol® 974P.

9. The aqueous pharmaceutical composition according to claim 7, wherein said aqueous solution comprises approximately 15% to 25% by weight (w/w) of poloxamer 407.

10. The aqueous pharmaceutical composition according to claim 7, wherein the pH of said aqueous solution is between about 7.0 and 8.0.

11. The aqueous pharmaceutical composition according to claim 7, wherein said aqueous solution further comprises a buffering agent selected from sodium phosphate monobasic, sodium phosphate dibasic, and sodium chloride, or a combination thereof.

12. The aqueous pharmaceutical composition according to claim 7, wherein said active agent is present in approximately 0.1% to 5% w/v.

13. The aqueous pharmaceutical composition according to claim 7 comprising:

(1) a crystalline Compound I having the formula:

Compound I

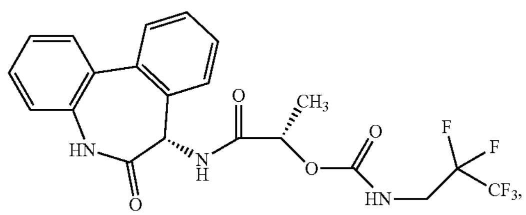

characterized by an x-ray powder diffraction pattern with peaks at 8.2, 13.8, 14.0, 18.4, and 20.9±0.15 degrees two-theta; and (2) a pharmaceutically acceptable aqueous solution comprising approximately 15% to 25% by weight (w/w) of poloxamer 407, wherein the pH is between about 7.0 and 8.0; and wherein said crystalline Compound I is present in approximately 0.01% to 20% w/v of said aqueous solution.

14. The aqueous pharmaceutical composition according to claim 13 wherein said aqueous solution comprises approximately 15% to 18% by weight of poloxamer 407, and wherein said crystalline Compound I is present in approximately 0.1% to 5% w/v.

15. The aqueous pharmaceutical composition according to claim 7 comprising:

(1) crystalline Compound II having the formula:

Compound II

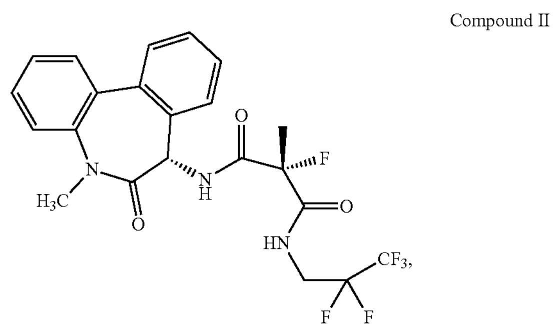 [SMILES: CN1C(=O)[C@@H](NC(=O)[C@](C)(F)C(=O)NCC(F)(F)C(F)(F)F)c2ccccc2-c2ccccc21]

characterized by an x-ray powder diffraction pattern with peaks at 8.4, 15.2, 16.0, 20.6, and 22.6±0.15 degrees two-theta; and (2) a pharmaceutically acceptable aqueous solution comprising approximately 15% to 25% by weight (w/w) of poloxamer 407, wherein the pH is between about 7.0 and 8.0; and wherein said crystalline Compound II is present in approximately 0.01% to 20% w/v of said aqueous solution.

16. The aqueous pharmaceutical composition according to claim 15 wherein said aqueous solution comprises approximately 15% to 18% by weight of poloxamer 407, and wherein said crystalline Compound II is present in approximately 0.1% to 5% w/v.

17. A method for the treatment of otic disorders which comprises intratympanic administration of a therapeutically effective amount of an active agent selected from:

a crystalline Compound I having the formula:

Compound I characterized by an x-ray powder diffraction pattern with peaks at 8.2, 13.8, 14.0, 18.4, and 20.9±0.15 degrees two-theta; or a crystalline Compound II having the formula:

Compound II

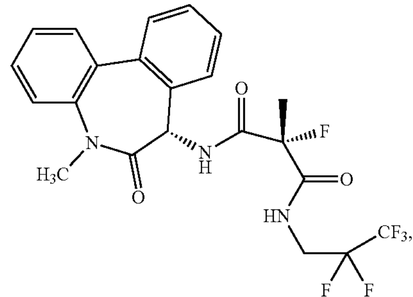

characterized by an x-ray powder diffraction pattern with peaks at 8.4, 15.2, 16.0, 20.6, and 22.6±0.15 degrees two-theta, to a patient in need thereof.

18. The method of claim 17, wherein the otic disorder is hearing loss.

19. The aqueous pharmaceutical composition of claim 7, wherein the aqueous pharmaceutical composition is formulated for intratympanic administration.

20. The aqueous pharmaceutical composition of claim 7, wherein the pharmaceutically acceptable aqueous solution comprises:

(A) approximately 15% to 25% by weight (w/w) of poloxamer 407; or (B) (i) approximately 15% to 25% by weight (w/w) of poloxamer 407 and (ii) approximately 0.5% to 4% by weight (w/w) of hydroxypropyl methylcellulose having a nominal viscosity of 40-60 cP or grade 80-120 cP; or (C) (i) approximately 10%-20% by weight (w/w) of poloxamer 407, and (ii) approximately 0.1%-0.3% by weight (w/w) of Carbopol® 974P; or (D) (i) approximately 0.5% to 8% by weight (w/w) of a hyaluronic acid; or (E) (i) approximately 0.5% to 4% by weight (w/w) of a hyaluronic acid, and (ii) approximately 5% to 20% by volume of polyethylene glycol 400.

21. The method of claim 20, wherein said active agent is present in approximately 0.01% to about 20% w/v of said aqueous solution.

22. The method of claim 17, wherein the intratympanic administration is intratympanic injection.

23. The method of claim 22, wherein the intratympanic injection is administered at or near the round window membrane in the ear of said patient.

24. The method of claim 17, wherein the otic disorder is selected from the group consisting of hearing loss, deafness, and conditions associated with vestibular dysfunction.

* * * * *